US010918285B2

(12) United States Patent
Yamanari

(10) Patent No.: US 10,918,285 B2
(45) Date of Patent: Feb. 16, 2021

(54) OPTICAL COHERENCE TOMOGRAPHIC DEVICE

(71) Applicant: Tomey Corporation, Nagoya (JP)

(72) Inventor: Masahiro Yamanari, Nagoya (JP)

(73) Assignee: TOMEY CORPORATION, Nagoya (JP)

( * ) Notice: Subject to any disclaimer, the term of this patent is extended or adjusted under 35 U.S.C. 154(b) by 863 days.

(21) Appl. No.: 15/668,765

(22) Filed: Aug. 4, 2017

(65) Prior Publication Data

US 2018/0035894 A1    Feb. 8, 2018

(30) Foreign Application Priority Data

Aug. 5, 2016  (JP) .............................. JP2016-154112
Oct. 13, 2016  (JP) .............................. JP2016-201911

(51) Int. Cl.
  *A61B 5/00* (2006.01)
  *A61B 3/10* (2006.01)
  *G01B 9/02* (2006.01)

(52) U.S. Cl.
  CPC ............ *A61B 5/0066* (2013.01); *A61B 3/102* (2013.01); *A61B 5/7203* (2013.01); *G01B 9/02027* (2013.01); *G01B 9/02041* (2013.01); *G01B 9/02055* (2013.01); *G01B 9/02083* (2013.01); *G01B 9/02091* (2013.01)

(58) Field of Classification Search
  CPC ............ G01B 9/02091; G01B 9/02027; G01B 9/02041; G01B 9/02055; G01B 9/02083; A61B 3/102; A61B 5/066; A61B 5/7203
  See application file for complete search history.

(56) References Cited

U.S. PATENT DOCUMENTS

| 9,863,869 B2 * | 1/2018 | Yasuno | G01B 9/02083 |
| 2009/0180093 A1 * | 7/2009 | Arai | G03B 27/72 |
| | | | 355/67 |
| 2009/0247862 A1 * | 10/2009 | Meyer | A61B 3/102 |
| | | | 600/425 |

(Continued)

FOREIGN PATENT DOCUMENTS

| JP | 4344829 A | 10/2009 |
| JP | 2013-019773 A | 1/2013 |
| WO | 2010122118 A1 | 10/2010 |

OTHER PUBLICATIONS

Erich Gotzinger et al. "Retinal pigment epithelium segmentation by polarization sensitive optical coherence tomography", Optics Express, vol. 16, No. 21, p. 16416-16428 (2008).

(Continued)

*Primary Examiner* — Dominic J Bologna
(74) *Attorney, Agent, or Firm* — Shumaker, Loop & Kendrick, LLP

(57) ABSTRACT

An optical coherence tomographic device configured to acquire a tomographic image of a subject by using an optical interferometry is provided. The optical coherence tomographic device include: a detector configured to detect interference light acquired by the optical interferometry, and to output an interference signal of the interference light; and a processor configured to calculate von Neumann entropy of noise components by using the noise components and signal intensities of the interference signals corresponding to at least one interference light detected by the detector.

14 Claims, 13 Drawing Sheets

(56) References Cited

U.S. PATENT DOCUMENTS

2014/0115022 A1   4/2014  Yasuno et al.
2016/0313112 A1*  10/2016 Yamanari ........... G01B 9/02075

OTHER PUBLICATIONS

Shuichi Makita et al. "Degree of polarization uniformity with high noise immunity using polarization-sensitive optical coherence tomography", Optics Letters, vol. 39, No. 24, p. 6783-6786 (2014).
Norman Lippok et al. "Degree of polarization (uniformity) and depolarization index: unambiguous depolarization contrast for optical coherence tomography", Optics Letters, vol. 40, No. 17, p. 3954-3057, (2015).

* cited by examiner

OPTICAL COHERENCE TOMOGRAPHIC DEVICE

TECHNICAL FIELD

The present disclosure relates to a device which performs optical tomographic imaging by means of optical coherence tomography. In particular, the present disclosure relates to a device which performs optical tomographic imaging including a correction process for improving the accuracy of data measured by polarization-sensitive optical coherence tomography.

BACKGROUND ART

Optical coherence tomography (OCT) is a widely used means to acquire high-resolution tomographic images of biological tissues and surgical nonbiological material particularly in ophthalmology because of the capability of noninvasive and noncontact measurement.

Several approaches of the OCT implementation are known, such as time domain OCT, called a time domain method, in which an optical path length of reference light is mechanically changed by translating a mirror; spectral domain OCT, called a Fourier domain method, in which tomographic images are acquired by detecting spectrum information with a spectrometer, and optical frequency sweeping-source OCT, also called a Fourier domain method, in which tomographic images are acquired by detecting a spectral interference signal with a wavelength-sweeping light source.

Form birefringence that changes a state of polarization is found in highly organized tissues with fiber bundles or molecules. In ocular tissues, retinal nerve fiber, vessel wall, sclera and trabecular meshwork are known to have the form birefringence. In addition, retinal pigment epithelium has a polarization scrambling effect because of melanin pigment. Polarization-sensitive OCT (PS-OCT) can measure the birefringence and polarization scrambling in such tissues, and various types of PS-OCT have been developed in recent years.

In PS-OCT, a measurement light typically has a circular polarization or modulated polarization, and two orthogonal polarizations of the interference are typically detected.

Japanese Patent No. 4344829 discloses one example of the PS-OCT implementations was disclosed. It described that the state of polarization was modulated by an electro-optic modulator along the transversal B-scan on the sample. The modulated light was split to a sample arm and a reference arm, and horizontal and vertical polarizations of the interfered light was detected spectrally. Jones matrix that indicates a polarization property of the sample was calculated from the measured data.

Japanese Patent Application Publication No. 2013-019773 discloses a method for estimating a phase retardation so that a bias by random noise was removed using a conversion table created by Monte Carlo simulation.

International Publication No. WO2010/122118 and "Retinal pigment epithelium segmentation by polarization sensitive optical coherence tomography" OPTICS EXPRESS, VOL. 16, No. 21, 2008, p 16416-16428 discloses a method for detecting the retinal pigment epithelial layer using a degree of polarization uniformity, which was derived from Stokes parameters measured by PS-OCT.

"Degree of polarization uniformity with high noise immunity using polarization-sensitive optical coherence tomography" OPTICS LETTERS, VOL. 39, No. 24, 2014, p 6783-6786, discloses a method for removing a bias of the degree of polarization uniformity caused by random noise using correction terms in Stokes parameters.

"Degree of polarization (uniformity) and depolarization index: unambiguous depolarization contrast for optical coherence tomography" OPTICS LETTERS, VOL. 40, No. 17, 2015, p 3954-3957, disclosed a dependency of the degree of polarization uniformity on the incident state of polarization, and introduced a depolarization index that does not depend on the incident state of polarization.

SUMMARY

"Degree of polarization uniformity with high noise immunity using polarization-sensitive optical coherence tomography", OPTICS LETTERS, VOL. 39, NO. 24, 2014, p 6783-6786, showed a method to remove the bias in Stokes parameters using the correction terms, thereby removing the bias in the degree of polarization uniformity. However, this approach could not resolve an issue that the degree of polarization uniformity depended on the incident state of polarization regardless of the bias caused by the random noise as indicated by "Degree of polarization (uniformity) and depolarization index: unambiguous depolarization contrast for optical coherence tomography" OPTICS LETTERS, VOL. 40, NO. 17, 2015, p 3954-3957.

"Degree of polarization uniformity with high noise immunity using polarization-sensitive optical coherence tomography" OPTICS LETTERS, VOL. 39, NO. 24, 2014, p 6783-6786, showed a method to calculate weighted summation of the degree of polarization uniformity for two incident orthogonal states of polarization. However, it did not discuss whether the dependency of the degree of polarization uniformity on the incident state of polarization is removed, nor show any mathematical evidence.

"Degree of polarization (uniformity) and depolarization index: unambiguous depolarization contrast for optical coherence tomography" showed a method to evaluate the depolarization using the depolarization index that was derived from Mueller matrix measured by PS-OCT. Although the depolarization index had no dependence on the incident state of polarization, it did not provide any solution for the bias caused by random noise.

To overcome these issues, this invention focuses on von Neumann entropy. It provides optical coherence tomographic device that can show randomness of polarization property of the sample using von Neumann entropy without the dependency on the incident state of polarization or the bias by noise. In addition, it also provides a method to mitigate a bias caused by small number of sampling points.

Solution to Technical Problem

An optical coherence tomography disclosed herein is configured to acquire a tomographic image of a subject by using an optical interferometry. The optical coherence tomographic device comprises: a detector configured to detect interference light acquired by the optical interferometry, and to output an interference signal of the interference light; and a processor configured to calculate von Neumann entropy of noise components by using the noise components and signal intensities of the interference signals corresponding to at least one interference light detected by the detector.

Further, an optical coherence tomography disclosed herein is configured to acquire a tomographic image of a subject by using an optical interferometry. The optical coherence tomographic device comprising: a detector configured to detect interference light acquired by the optical interferometry, and to output an interference signal of the interference light; and a processor configured to calculate covariance matrix that indicates a polarization property of the subject based on the interference signal outputted by the detector, and to calculate von Neumann entropy based on the calculated covariance matrix, wherein the processor is configured to, when a number of samples of an ensemble average of the covariance matrix to be used for calculation is insufficient, correct an eigenvalues of the ensemble averaged covariance matrix, and calculate the von Neumann entropy by using the corrected eigenvalues.

Further, an optical coherence tomography disclosed herein is configured to acquire a tomographic image of a subject by using an optical interferometry. The optical coherence tomographic device comprising: a detector configured to detect interference light acquired by the optical interferometry, and to output an interference signal of the interference light; and a processor configured: to measure Jones matrices that indicate a polarization property of the subject based on the interference signal outputted by the detector; perform a moving average process relative to the measured Jones matrices; perform the moving average process relative to covariance matrices of Jones matrices that has been subjected to the moving average process; and estimate the Jones matrix by using eigenvalue decomposition; and calculate von Neumann entropy by using the eigenvalue decomposition.

The correction process in this invention is implemented using a theory of Cloude-Pottier decomposition. Namely, measured Jones matrix that shows polarization property of the sample is vectorized through a complete basis set, for example, Pauli basis set or lexicographic ordering basis set. After the vectorization, the dimension is expanded, for example, from 1×4 vector to 4×4 coherency matrix or covariance matrix. The expanded 4×4 coherency or covariance matrix is then ensemble averaged and diagonalized to obtain the eigenvalues and eigenvectors. Von Neumann entropy can be obtained using the eigenvalues.

As described, the optical coherence tomographic device of this invention can show randomness of the polarization property of the sample independent of the incident state polarization and can correct the bias of von Neumann entropy caused by the noise.

DESCRIPTION OF EMBODIMENTS

Figure 1:
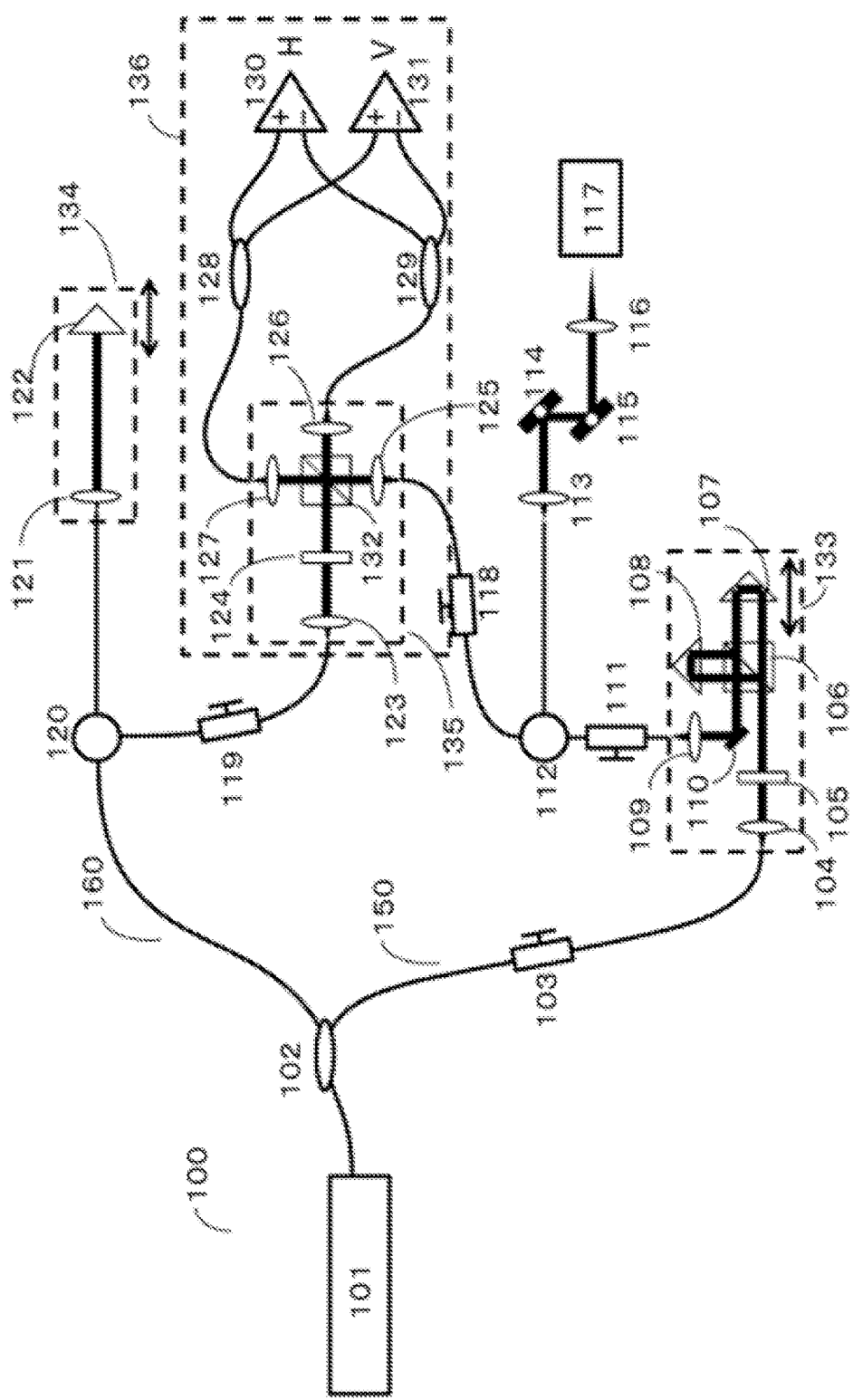
FIG. 1 is a diagram showing a configuration of an optical system of an optical coherence tomographic device according to a present disclosure.

An optical coherence tomographic device according to one embodiment of the present disclosure will be described with reference to drawings. FIG. 1 shows details of a configuration of a tomographic image acquisition section 100.

As shown in FIG. 1, the tomographic image acquisition section 100 acquires two-dimensional and/or three-dimensional tomographic images by illuminating a sample 117 (subject) with measurement light. In the present embodiment, Fourier domain or swept-source OCT using a frequency-swept light source 101 which allows sweeping with a temporally changing frequency, is employed.

That is, light emitted from the frequency-swept light source 101 is directed to a fiber coupler 102 through an optical fiber, and is split into a reference arm 160 and a sample arm 150 at the fiber coupler 102 at a ratio of 5:95, for example. The reference light in the reference arm 160 is directed to an optical circulator 120, a collimating lens 121, and thereafter enters a reference mirror 122. Movement of the reference mirror 122 on an optical axis can be controlled for optical path length adjustment to adjust a reference light path onto a surface position of the sample. In advance of measurement of the OCT tomographic image, a measurement light path length is adjusted to a reference light path length.

The reference light reflected by the reference mirror 122 passes through the collimating lens 121, the optical fiber. The optical path of the reference light is changed by the optical circulator 120. Then the reference light passes through a polarization controller 199 and a collimating lens 123, and then is directed to a polarization-sensitive detection arm 136.

On the other hand, the measurement light that is split at the fiber coupler 102 and outputted to the sample arm 150 passes through a polarization controller 103, and is directed to a collimating lens 104 and thereafter passes through a polarizer 105 of a polarization-dependent delay line 133. In the present embodiment, a polarization angle of the polarizer 105 is set at 45 degrees. Further, the polarization angle of the measurement light after passing through the polarization controller 103 and immediately before entering the collimator lens 104 is also controlled at 45 degrees. Thus, in order to efficiently take the measurement light polarized at 45 degrees, the polarization controller 103 and the polarizer 105 are adjusted and controlled.

The measurement light polarized at 45-degrees passes through a beam splitter 106 provided in the polarization-dependent delay uni133, to be split into two light beams in different linear polarization states (horizontal direction and vertical direction) which are orthogonal to each other. The split light beams of the measurement light are reflected by different right-angle prisms 107 and 108, and propagated through two different optical paths, respectively. A delay is generated between the two different polarization states (horizontal direction and vertical direction) by controlling movement of one or both of the right-angle prisms 107 and 108.

The reflected lights at the right-angle prisms 107 and 108 are directed to the polarizing beam splitter 106 again at laterally shifted incident location, directed to a mirror 110, and coupled to an optical fiber using a collimating lens 109.

The light output from the polarization-dependent delay line 133 is directed to a polarization controller 111, an optical circulator 112, a collimating lens 113, a galvanometer scanner mirrors 114 and 115, an objective lens 116 to focus on the sample 117.

The galvanometer scanner mirrors 114 and 115 are used to scan the measurement light on the sample in horizontal and vertical directions. Using these scanning mirrors, two- or three-dimensional tomographic images are acquired.

A backscattered light from the sample 117 is directed to the lens 116, the galvanometer scanner mirrors 115 and 114, and the collimating lens 113, the optical circulator 112, a polarization controller 118, and a collimating lens 125 to input the light to the polarization-sensitive detection arm.

The reference light that is input from the collimating lens 123 through a polarizer 124 and the measurement light that comes from the sample 117 are combined at a non-polarizing beam splitter 132. Two output lights from the beam splitter 132 are coupled to optical fibers through collimating lenses 126 and 127, and directed to inline polarizing beam splitters 128 and 129 to divide two orthogonal components of the polarization.

Here, an angle of the polarizer 124 is set to be 45 degrees to equalize the optical powers of horizontal and vertical polarizations after the inline polarizing beam splitters 128 and 129. In addition, the polarization controller 119 is controlled to optimize the output power at the polarizer 124.

Figure 2:
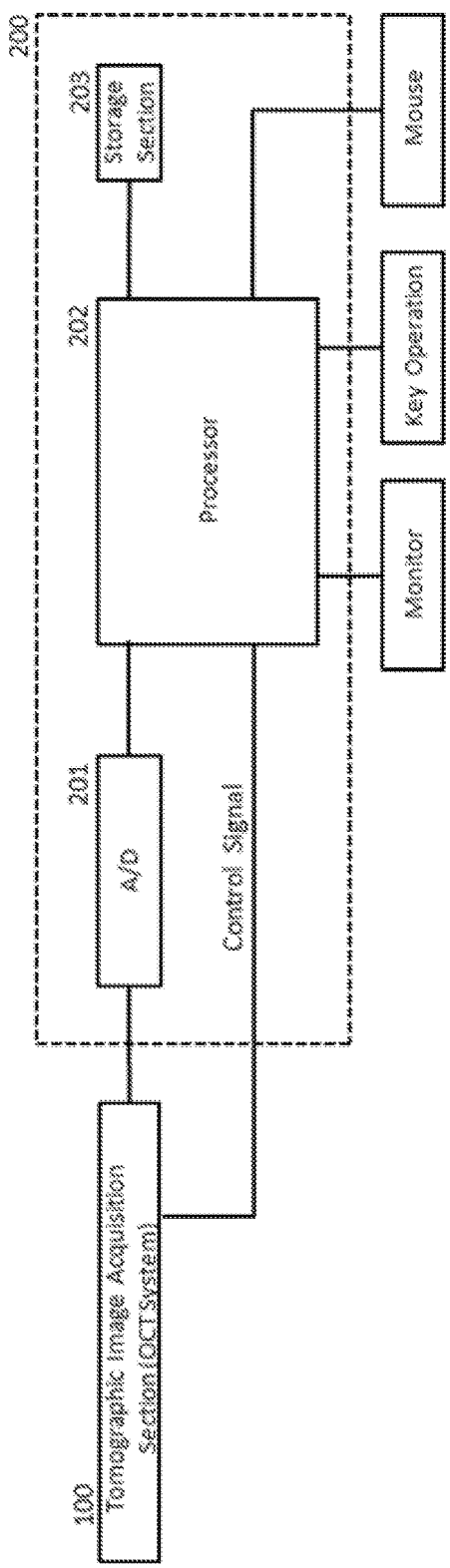
FIG. 2 is a block diagram showing a configuration of the optical coherence tomographic device according to the present disclosure.

The interfered signals of horizontal and vertical polarizations are detected by two balanced receivers 130 and 131, respectively. The detected interference signals are processed such as with Fourier transform at a processing unit 201 in a control unit 200 of FIG. 2. The processing outputs B-scan and/or C-scan images from the volumetric Jones matrix data of the sample 117, and saves the images and data in a storage 203.

Figure 4A:
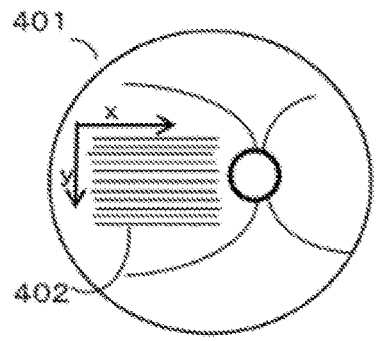
FIGS. 4A to 4C are diagrams for explaining a flow of acquiring a three-dimensional tomographic image according to the present disclosure.
Figure 4B:
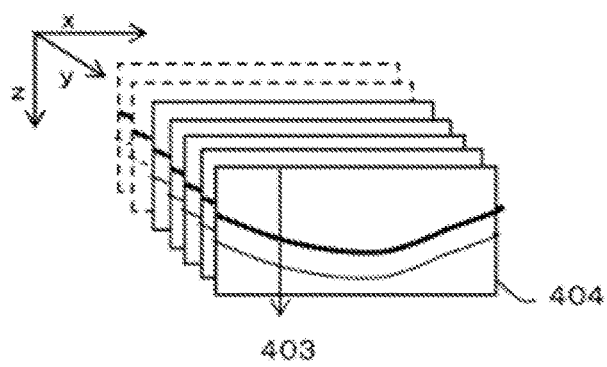
Figure 4B:
Figure 4C:
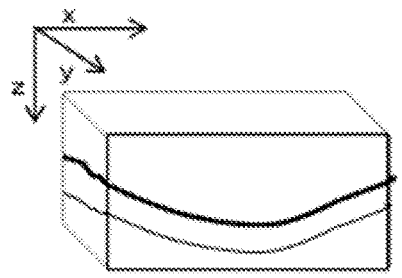

FIGS. 4A to 4C shows a schematic protocol to acquire tomographic images at the tomographic imaging system 100. FIGS. 4A, B and C show schematics of a representative retina of an eye E under observation, several B-scan images and how the C-scan image is extracted from the volumetric data, respectively. In FIGS. 4A, B and C, the x, y, and z axes indicate the direction of the B-scan, the direction of the C-scan, and the axial depth of the A-scan, respectively.

404 in FIG. 4B shows the two-dimensional tomographic image with a transversal scan in x direction by the galvanometer mirror 106, which is calculated from the A-scan signals of 403 by the processing unit 202.

Figure 3:
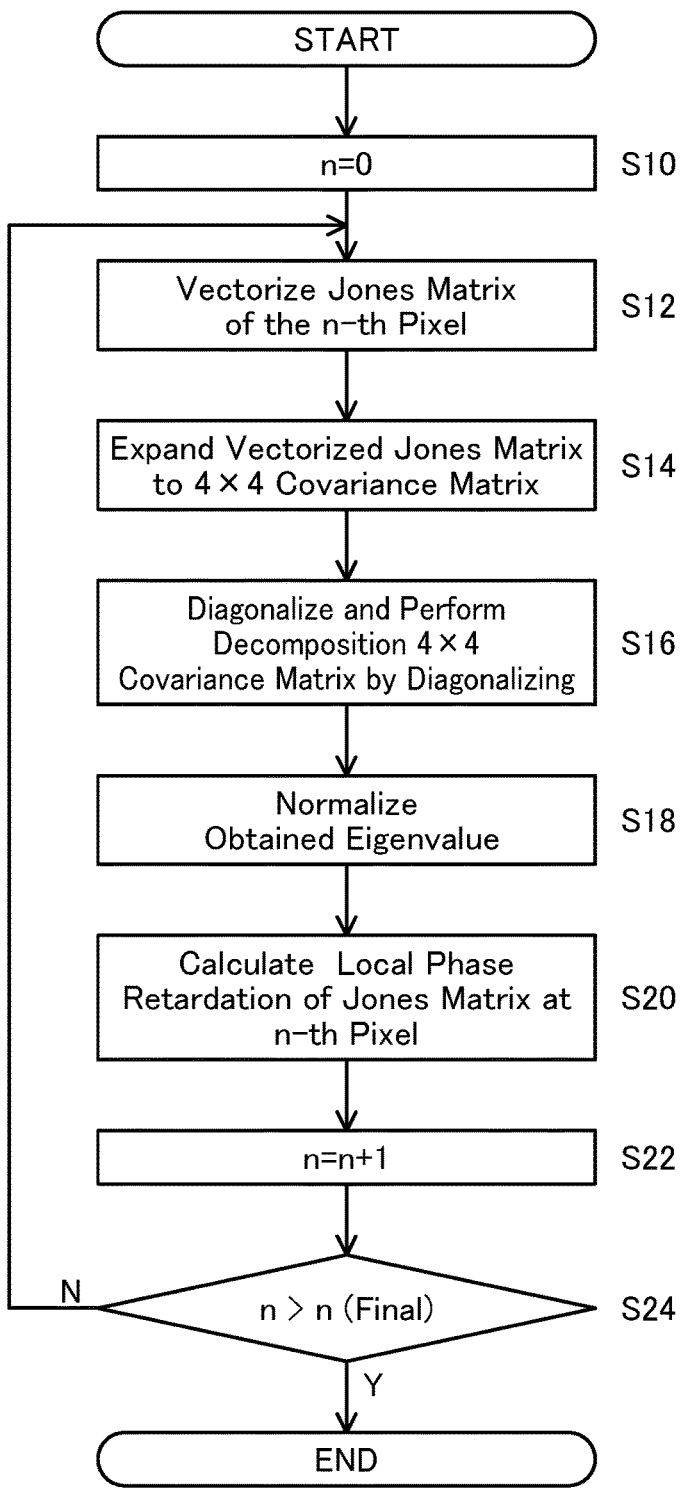
FIG. 3 is a flowchart of a process to acquire a three-dimensional tomographic image according to the present disclosure.

Next, the method to obtain expected values of individual elements of Jones matrices in B-scan images and/or C-scan images of volumetric data measured from the sample 117 will be described with reference to a flowchart shown in FIG. 3.

A first pixel is set in S10. The first pixel is defined as a 0-th pixel in S10, and the set pixel is defined as an n-th pixel.

Next, the measured Jones matrix is vectorized in S12. The measured Jones matrix is defined as:

$$J = [\underline{E_1} \ \underline{E_2}] = \begin{bmatrix} J_{1H} & J_{2H} \\ J_{1V} & J_{2V} \end{bmatrix} \quad \text{[Equation 1]}$$

where the first and second columns are Jones vectors measured with orthogonally polarized incident light, respectively. Eq. 1 is then rearranged to a 1×4 target vector as:

$$\underline{\kappa} = \tfrac{1}{2} Tr(J\Psi) \quad \text{[Equation 2]}$$

where Tr(JΨ) shows a trace of a matrix JΨ, and Ψ shows an arbitrary complete basis set. The target vector is defined using all elements of the basis.

As the representative examples of the complete basis sets, Pauli basis set:

$$\{\Psi_P\} = \quad \text{[Equation 3]}$$
$$\left\{ \sqrt{2}\begin{bmatrix}1 & 0\\0 & 1\end{bmatrix} \ \sqrt{2}\begin{bmatrix}0 & 1\\0 & -1\end{bmatrix} \ \sqrt{2}\begin{bmatrix}0 & 1\\1 & 0\end{bmatrix} \ \sqrt{2}\begin{bmatrix}0 & -j\\j & 0\end{bmatrix} \right\}$$

and lexicographic ordering basis set:

$$\{\Psi_L\} = \left\{ 2\begin{bmatrix}1 & 0\\0 & 0\end{bmatrix} \ 2\begin{bmatrix}0 & 1\\0 & 0\end{bmatrix} \ 2\begin{bmatrix}0 & 0\\1 & 0\end{bmatrix} \ 2\begin{bmatrix}0 & 0\\0 & 1\end{bmatrix} \right\} \quad \text{[Equation 4]}$$

can be used. If Ψ is a complete basis set, equivalent results are obtained for any Ψ. If the lexicographic ordering basis set is used here, the target vector can be shown as:

$$\underline{\kappa}_L = [J_{1H} J_{2H} J_{1V} J_{2V}]^T \quad \text{[Equation 5]}$$

where T shows a transpose of the vector.

Next, the vectorized Jones matrix is expanded to 4×4 coherency or covariance matrix in S14. The target vector k in Eq. 2 can be statistically modeled as multivariate complex Gaussian distribution. A probability density function of the target vector k is shown as:

$$p(\underline{\kappa}) = \frac{1}{\pi^m \det(C)} \exp(-\underline{\kappa}^\dagger C^{-1} \underline{\kappa}) \quad \text{[Equation 6]}$$

where det (C) shows a determinant of a matrix C, m shows a dimension of the target vector $\underline{\kappa}$. In Eq. 5, m=4. The superscript dagger shows a transposed conjugate. The matrix C is a semidefinite covariance matrix, and defined as:

$$C = E\{\kappa\kappa^\dagger\} \quad \text{[Equation 7]}$$

where E{κκ†} shows an expected value of κκ†. The matrix C can be estimated as:

$$Z = \frac{1}{n}\sum_{i=1}^{n} \kappa_i \kappa_i^\dagger \quad \text{[Equation 8]}$$

where Eq. 8 is a maximum likelihood estimation of the matrix C, n shows a number of samples, and κi is the i-th target vector in n samples. Equation 8 has a complex Wishart distribution, and the probability density function is shown as:

$$p(Z) = \frac{n^{mn}[\det(Z)]^{n-m}}{[\det(C)]^n \tilde{\Gamma}_m(n)} \exp[-nTr(C^{-1}Z)] \quad \text{[Equation 9]}$$

where the following equation is used:

$$\tilde{\Gamma}_m(n) = \pi^{m(m-1)/2} \prod_{i=1}^{m} \Gamma(n-i+1) \quad \text{[Equation 10]}$$

$\Gamma(n-i+1)$ is a gamma function.

In this embodiment, Z, which is defined in Eq. 8, is expanded to 4×4 covariance matrix T using the lexicographic ordering basis set as:

$$T \equiv \overline{\underline{\kappa}_L \underline{\kappa}_L^\dagger} = \begin{bmatrix} \overline{|J_{1H}|^2} & \overline{J_{1H}J_{2H}^*} & \overline{J_{1H}J_{1V}^*} & \overline{J_{1H}J_{2V}^*} \\ \overline{J_{2H}J_{1H}^*} & \overline{|J_{2H}|^2} & \overline{J_{2H}J_{1V}^*} & \overline{J_{2H}J_{2V}^*} \\ \overline{J_{1V}J_{1H}^*} & \overline{J_{1V}J_{2H}^*} & \overline{|J_{1V}|^2} & \overline{J_{1V}J_{2V}^*} \\ \overline{J_{2V}J_{1H}^*} & \overline{J_{2V}J_{2H}^*} & \overline{J_{2V}J_{1V}^*} & \overline{|J_{2V}|^2} \end{bmatrix}$$  [Equation 11]

where the overline shows an ensemble average. In the ensemble average, it is assumed that the measured target is static in a wide sense and has ergodicity in a region of interest. Namely, the ensemble average can be applied spatially or temporarily, or both spatially and temporarily.

From the definition of Eq. 11, T is also the semidefinite matrix as well as C and Z. If Pauli basis set is used as $\Psi$, a covariance matrix has a same form as Mueller matrix. Hence, the covariance matrix to be described later can be interpreted as Mueller matrix in this case. Moreover, in OCT, a Jones vector and Stokes vector of each A-scan are interchangeable, it is possible to use Stokes vector instead of Jones vector by conversion process.

Next, the expanded 4×4 covariance matrix T is diagonalized and decomposed in S16. If Cloude-Pottier decomposition is used, the 4×4 covariance matrix T is decomposed by diagonalization as:

$T = UAU^\dagger$ $A = \mathrm{diag}[\lambda_1, \lambda_2, \lambda_3, \lambda_4], \lambda_1 \geq \lambda_2 \geq \lambda_3 \geq \lambda_4 \geq 0$ $U = [\underline{e}_1 \underline{e}_2 \underline{e}_3 \underline{e}_4]$  [Equation 12]

where the matrix A is a diagonal matrix composed by four eigenvalues, and the matrix U is an unitary matrix composed by four 1×4 eigenvectors. The inequality of the eigenvalues can be derived from a fact that T is a semidefinite matrix.

In S18, the eigenvalues of Eq. 12 are normalized as Eq. 13 as $$\lambda_i' = \frac{\lambda_i}{\sum_j^4 \lambda_j}, \quad i = 1, 2, 3, 4$$  [Equation 13]

so that $0 \leq \lambda_i' \leq 1$. The normalized eigenvalue $\lambda_i'$ can be regarded as a probability that the corresponding eigenvector $\underline{e}_i$ occurs in a sense of multinomial process.

The local phase retardation is obtained in S20. In a case where lexicographic ordering basis set $\{\Psi_L\}$ as shown in Eq. 4 is used, $\underline{e}_i := [a_i b_i c_i d_i]^T$  [Equation 14]

the eigenvector $\underline{e}_i$ is rearranged to a Jones matrix $L_i$ as:

$$L_i = \begin{bmatrix} a_i & b_i \\ c_i & d_i \end{bmatrix}$$  [Equation 15]

As described above, this incoherent approach to derive $L_i$ by Cloude-Pottier decomposition is applicable for the measured Jones matrix in Eq. 1. However, the Eq. 1 does not show the local polarization property of the sample, because all influences before and after the backscattering and reflecting at the sample is accumulated in Eq. 1 along the depth. The cumulative attribute can be eliminated by calculating a local Jones matrix. Instead of the cumulative Jones matrix in Eq. 1, Eq. 16 is used as the local Jones matrix as shown in the following, where the data is processed by optical frequency dependence (k-dependence) correction.

$$\hat{E}'^{-1}_{sample}\left(z - \frac{\delta z}{2}\right)\hat{E}'_{sample}\left(z + \frac{\delta z}{2}\right) =$$  [Equation 16]
$$J_{in}'^{-1} U_s^{-1}(z) \begin{bmatrix} \lambda_1(\delta z)|_z & 0 \\ 0 & \lambda_2(\delta z)|_z \end{bmatrix} U_s(z) J_{in}'$$

where E'$_{sample}$ (^ is attached above "E") indicates the Jones matrix calculated with k-dependence correction, where two Jones matrices with a depth separation of $\delta z$ centered at z are used. Us(z) shows the Jones matrix that indicates cumulative optic axis of the sample at the depth z, and $\lambda_1(\delta z)|_z$ and $\lambda_2(\delta z)|_z$ show two eigenvalues of the local Jones matrix with a depth separation of $\delta z$ centered at z. Jin' shows the Jones matrix that indicates the polarization property from the incident fiber-optic illumination system to the surface of the sample.

Since a product of two multivariate Gaussian distributions is also a multivariate Gaussian distribution, the statistical description in the above also holds for the local Jones matrix. In the case of the local Jones matrix, it was weighed as Eq. 17, $$\frac{\sqrt{\left\|\hat{E}'_{sample}\left(z-\frac{\delta z}{2}\right)\right\|_2 \left\|\hat{E}'_{sample}\left(z+\frac{\delta z}{2}\right)\right\|_2}}{\left\|\hat{E}'^{-1}_{sample}\left(z-\frac{\delta z}{2}\right)\right\|_2 \left\|\hat{E}'_{sample}\left(z+\frac{\delta z}{2}\right)\right\|_2}$$  [Equation 17]
$$\hat{E}'^{-1}_{sample}\left(z - \frac{\delta z}{2}\right)\hat{E}'_{sample}\left(z + \frac{\delta z}{2}\right)$$

where $|X|_2$ denotes an operator norm of the matrix X. After it was weighed in Eq. 17, the ensemble average processing shown in Eq. 11 is performed to estimate the local Jones matrix. The Cloude-Pottier decomposition is then used to obtain Eq. 15 of the local Jones matrix. A local phase retardation $R_i$ of $L_i$ is derived as Eq. 18, $R_i = \arg(\xi_1^{(i)} \xi_2^{(i)*})$  [Equation 18]

where $\xi_1^{(i)}$ and $\xi_2^{(i)}$ are the eigenvalues of $L_i$, and $\arg(x)$ denotes the argument of the complex value x.

Assuming that the sample has a dominant scattering mechanism, $L_1$ and $R_1$ that are paired up with the largest eigenvalue $\lambda_1$ can be regarded as the Jones matrix and the local phase retardation of the dominant scattering mechanism, respectively. In addition, when the sample is modeled as multinomial process, an expected value of the phase retardation can be defined as Eq. 19, $$E(R) = \sum_i \lambda_i' R_i$$  [Equation 19]

In addition, optic axis of $L_i$ is derived from an eigenvector that is paired to $\xi_1^{(i)}$. The eigenvector is converted to Stokes vector, and the angle relative to a reference can be calculated.

As described above, after deriving the local retardation at n-th pixel in S20, in S22 n=n+1 is set, and the local retardation at the next pixel is also derived by processing in S12 to S20.

After deriving the local retardation for all pixels in S24 (n>n (Final)), a series of the processing is completed. As described above, the expected value of the local retardation of Jones matrix is obtained, and the Jones matrix is appropriately estimated by using the expected value, and thereby quantitative analysis of the sample becomes possible.

To show a degree of randomness of the Jones matrix in a region of interest, von Neumann entropy is derived as the following. In general, the logarithmic base of the entropy can be defined arbitrarily. In this embodiment, the logarithmic base is set to be m=4 so that $0 \leq H \leq 1$. When H=0, the sample has completely homogeneous Jones matrix. When H=1, the sample has a completely random Jones matrix. In practice, the measured entropy has a value between them.

$$H = \sum_i -\lambda_i' \log_4 \lambda_i' \quad \text{[Equation 20]}$$

Using the von Neumann entropy, a randomness of polarization property of a sample in a space can be obtained. Thus, the polarization scrambling effect derived from a melanin pigment amount of retinal pigment epithelium, iris pigment epithelium, and the uvea membrane can be evaluated, and the randomness of the polarization characteristic distribution in the tissues can be evaluated.

Since the von Neumann entropy shows randomness of the measured Jones matrix, it includes both polarization property of the subject and influence of the noise. When the signal-to-noise ratio (SNR) is low, the bias caused by the noise to the von Neumann entropy would be high, resulting in unreliable quantitative evaluation of the polarization property of the subject. To overcome this issue, the bias in the von Neumann entropy caused by the random noise is corrected as shown in the following.

As the first step, the bias correction for the non-localized cumulative Jones matrix shown in Eq. 1 will be described.

Since the random noise and the polarization property of the subject are independent, the additivity is satisfied as shown in Eq. 21. $H_{measured}$, $H_{subject}$ and $H_{noise}$ are the entropies of the measured data, the subject and the von Neumann entropy of the noise, respectively. Here, estimation method of removing $H_{noise}$ inform the $H_{measured}$ will be described.

$$H_{measured} = H_{subject} + H_{noise} \quad \text{[Equation 21]}$$

The 4×4 covariance matrix can be divided to two subspaces that are each related to $\underline{E_1}$ and $\underline{E_2}$. The von Neumann entropy satisfies the following inequality called subadditivity in Eq. 22.

$$H_{noise}(\underline{E_1},\underline{E_2}) \leq H_{noise}(\underline{E_1}) + H_{noise}(\underline{E_2}) \quad \text{[Equation 22]}$$

where $H_{noise}(\underline{E_1})$ and $H_{noise}(\underline{E_2})$ are the von Neumann entropies in the subspace, and $H_{noise}(\underline{E_1},\underline{E_2})$ is the explicit expression as a joint entropy of the noise in the covariance matrix.

Assuming that the noises in the subspaces of $\underline{E_1}$ and $\underline{E_2}$ are independent, Eq. 22 holds equality as shown in Eq. 23;

$$H_{noise}(\underline{E_1},\underline{E_2}) = H_{noise}(\underline{E_1}) + H_{noise}(\underline{E_2}) \quad \text{[Equation 23]}$$

Eq. 23 shows that the entropy of the noise in 4×4 covariance matrix can be derived from the summation of the entropies of the noises in the subspaces, namely, 2×2 covariance matrices. Nevertheless, it may be still difficult to utilize the pdfs of the covariance matrix and the eigenvalue to derive $H_{noise}$. Hence, we suggest yet another approach in the following.

$H_{noise}(\underline{E_1})$ and $H_{noise}(\underline{E_2})$ can be derived from the eigenvalues of the covariance matrix as shown in Eq. 24.

$$H_{noise}(\underline{E_i}) = \sum_{j=1}^{2} -\lambda_j^{(i)} \log_4(\lambda_j^{(i)}) \quad \text{[Equation 24]}$$

where $\zeta_j^{(i)}$ is the j-th eigenvalue of the subspace composed of $\underline{E_i}$. The eigenvalue has the following relationship with a degree of polarization (DOP) or a degree of polarization uniformity (DOPU) in the case of OCT;

$$\lambda_j^{(i)} = \frac{1 \pm P^{(i)}}{2} \quad \text{[Equation 25]}$$

where $P^{(i)}$ shows the DOPU of the subspace composed of $E_i$. Consequently, it turns out that $H_{noise}(\underline{E_1},\underline{E_2})$ can be derived if a relationship between the DOPU and the noise is derived.

Assuming that the calculated Jones matrix has an independent complex additive white Gaussian noise in each matrix element, the Jones matrix can be described as:

$$J_{measured} = [\underline{E_1} + \underline{n_1} \quad \underline{E_2} + \underline{n_2}] = \begin{bmatrix} E_{1H} + n_{1H} & E_{2H} + n_{2H} \\ E_{1V} + n_{1V} & E_{2V} + n_{2V} \end{bmatrix} = \begin{bmatrix} g_{1H} & g_{2H} \\ g_{1V} & g_{2V} \end{bmatrix} \quad \text{[Equation 26]}$$

Note that Eq. 26 is a cumulative Jones matrix along the depth that is characteristic to PS-OCT as described above. Stokes parameters of $[g_{1H} \; g_{1V}]^T$ in Eq. 26 are defined as:

$$\begin{bmatrix} s_0^{(1)} \\ s_1^{(1)} \\ s_2^{(1)} \\ s_3^{(1)} \end{bmatrix} = \begin{bmatrix} |g_{1H}|^2 + |g_{1V}|^2 \\ |g_{1H}|^2 - |g_{1V}|^2 \\ 2\text{Re}[g_{1H}g_{1V}^*] \\ 2\text{Im}[g_{1H}g_{1V}^*] \end{bmatrix} \quad \text{[Equation 27]}$$

and Stokes parameters of $[g_{2H} \; g_{2V}]^T$ are also defined similarly.

The Stokes parameters without the noise components are derived as Eq. 28.

$$\begin{bmatrix} s_0'^{(1)} \\ s_1'^{(1)} \\ s_2'^{(1)} \\ s_3'^{(1)} \end{bmatrix} := \begin{bmatrix} |E_{1H}|^2 + |E_{1V}|^2 \\ |E_{1H}|^2 - |E_{1V}|^2 \\ 2\text{Re}[E_{1H}E_{1V}^*] \\ 2\text{Im}[E_{1H}E_{1V}^*] \end{bmatrix} = \begin{bmatrix} |E_{1H}|^2 + |E_{1V}|^2 \\ |E_{1H}|^2 - |E_{1V}|^2 \\ 2|E_{1H}||E_{1V}|\cos\delta \\ 2|E_{1H}||E_{1V}|\sin\delta \end{bmatrix} \quad \text{[Equation 28]}$$

where $\delta = \arg[E_{1H}E_{1V}^*]$, and $\delta$ is influenced by polarization property of the subject but not influenced by the signal intensity. In addition, $\delta$ is eventually cancelled in $P^{(i)}$ as seen later. Thus, $\delta$ may be unknown.

Assuming that the Stokes parameters using ensemble averaged signal intensities are defined as:

$$\begin{bmatrix} s_0''^{(1)} \\ s_1''^{(1)} \\ s_2''^{(1)} \\ s_3''^{(1)} \end{bmatrix} := \begin{bmatrix} \overline{|g_{1H}|^2} + \overline{|g_{1V}|^2} \\ \overline{|g_{1H}|^2} - \overline{|g_{1V}|^2} \\ 2\text{Re}[\overline{g_{1H}g_{1V}^*}] \\ 2\text{Im}[\overline{g_{1H}g_{1V}^*}] \end{bmatrix} = \begin{bmatrix} \overline{|g_{1H}|^2} + \overline{|g_{1V}|^2} \\ \overline{|g_{1H}|^2} - \overline{|g_{1V}|^2} \\ 2\text{Re}[\overline{E_{1H}E_{1V}^*}] \\ 2\text{Im}[\overline{E_{1H}E_{1V}^*}] \end{bmatrix} =$$

[Equation 29]

$$= \begin{bmatrix} \overline{|g_{1H}|^2} + \overline{|g_{1V}|^2} \\ \overline{|g_{1H}|^2} - \overline{|g_{1V}|^2} \\ 2|\overline{E_{1H}}||\overline{E_{1V}}|\cos\delta \\ 2|\overline{E_{1H}}||\overline{E_{1V}}|\sin\delta \end{bmatrix}$$

$$= \begin{bmatrix} \overline{|g_{1H}|^2} + \overline{|g_{1V}|^2} \\ \overline{|g_{1H}|^2} - \overline{|g_{1V}|^2} \\ 2\sqrt{\overline{|g_{1H}|^2} - \overline{|n_{1H}|^2}}\sqrt{\overline{|g_{1V}|^2} - \overline{|n_{1V}|^2}}\cos\delta \\ 2\sqrt{\overline{|g_{1H}|^2} - \overline{|n_{1H}|^2}}\sqrt{\overline{|g_{1V}|^2} - \overline{|n_{1V}|^2}}\sin\delta \end{bmatrix}$$

and assuming that the signal amplitude is much higher than the noise amplitude for each element of the Jones matrix so that distributions of the measured amplitudes are Gaussian and that the polarization property of the subject has a symmetric pdf of the signal intensity so that it does not bias the ensemble average in Eq. 29. DOPU that shows the bias by the relative relationship between the signal intensity and noise power is derived as $$P^{(1)} = \frac{\sqrt{\{s_1''^{(1)}\}^2 + \{s_2''^{(1)}\}^2 + \{s_3''^{(1)}\}^2}}{s_0''^{(1)}}$$

[Equation 30]

$$= \frac{\sqrt{(\overline{|g_{1H}|^2} - \overline{|g_{1V}|^2})^2 + 4(\overline{|g_{1H}|^2} - \overline{|n_{1H}|^2})(\overline{|g_{1V}|^2} - \overline{|n_{1V}|^2})}}{\overline{|g_{1H}|^2} + \overline{|g_{1V}|^2}}$$

$P^{(2)}$ is also derived similarly. $H_{noise}$ is calculated from the measured signal intensities and noise powers. Note that Eq. 30 used ensemble averaged signal intensities but not ensemble averaged Stokes parameters. If each factor of the product at the second term in the square root of the numerator in Eq. 30 has a negative value, $P^{(1)}$ can become out of the defined range from 0 to 1. To avoid the undefined range, if each factor of the product at the second term in the square root of the numerator in Eq. 30 has a negative value, it can be replaced to 0, and then Eq. 30 can be calculated.

As described above, using Eqs. 23 to 25, 29 and 30, $H_{noise}$ is derived from the signal intensity and noise power. In this way, $H_{noise}$ can be removed from $H_{measured}$.

Although the equations above are effective for a certain axial depth, we have not considered cumulative attributes of the Jones matrix along the axial depth in PS-OCT. If a region of interest is set spatially including the axial direction, the resultant DOPU and entropy may have an artifact by high birefringence that changes the Jones matrices rapidly in the axial direction. Hence, $H_{noise}$ of the local Jones matrix is derived in the following.

To calculate the local Jones matrix, two Jones matrices that are axially separated by a length $\delta z$ centered at a depth $z$ are used. Using the same notations in Eqs. 16 and 17, all matrix elements are denoted by Eq. 31 by using similar notations in Eqs. 16 and 17.

$$\tilde{E}'_{sample}\left(z + \frac{\delta z}{2}\right) = \begin{bmatrix} a & b \\ c & d \end{bmatrix},$$

$$\tilde{E}'_{sample}\left(z - \frac{\delta z}{2}\right) = \begin{bmatrix} e & f \\ g & h \end{bmatrix}$$

[Equation 31]

The local Jones matrix is derived as Eq. 32.

$$\tilde{E}'^{-1}_{sample}\left(z - \frac{\delta z}{2}\right)\tilde{E}'_{sample}\left(z + \frac{\delta z}{2}\right) =$$

$$\left[\det\left(\tilde{E}'_{sample}\left(z - \frac{\delta z}{2}\right)\right)\right]^{-1}\begin{bmatrix} ha - fc & hb - fd \\ ga + ec & -gb + ed \end{bmatrix}$$

[Equation 32]

Since the determinant in Eq. 32 has the effect of distorting the noise floor of the matrix, it complicates the estimation of the entropy. Therefore, the following Eq. 33 is used instead of Eq. 32;

$$\det\left(\tilde{E}'^{-1}_{sample}\left(z - \frac{\delta z}{2}\right)\right)\tilde{E}'^{-1}_{sample}\left(z - \frac{\delta z}{2}\right)\tilde{E}'_{sample}\left(z + \frac{\delta z}{2}\right) =$$

$$\begin{bmatrix} ha - fc & hb - fd \\ ga + ec & -gb + ed \end{bmatrix} \equiv [\underline{\varepsilon_1} \ \underline{\varepsilon_2}] = \begin{bmatrix} \varepsilon_{1H} & \varepsilon_{2H} \\ \varepsilon_{1V} & \varepsilon_{2V} \end{bmatrix}$$

[Equation 33]

To calculate $H_{noise}$ of the local Jones matrix, Eq. 33 is used instead of Eq. 26, and the same procedure to calculate $P^{(1)}$ and $P^{(2)}$ shown in Eq. 30 is followed. Unlike Eq. 26, however, Eq. 33 does not satisfy the additivity in Eq. 23, because the first and second column vectors in Eq. 33 are dependent. In this case, Eq. 23 can be modified as Eq. 34.

$H_{noise}(\underline{\varepsilon_1},\underline{\varepsilon_2}) = H_{noise}(\underline{\varepsilon_1}) + H_{noise}(\underline{\varepsilon_2}) - H_{noise}(\underline{\varepsilon_1};\underline{\varepsilon_2})$ [Equation 34]

where the third term in the right side is mutual information of $\underline{\varepsilon_1}$ and $\underline{\varepsilon_2}$.

Equation 34 can be rearranged using a conditional entropy as Eq. 35.

$H_{noise}(\underline{\varepsilon_1};\underline{\varepsilon_2}) = H_{noise}(\underline{\varepsilon_1}) - H_{noise}(\underline{\varepsilon_1} \mid \underline{\varepsilon_2})$ $= H_{noise}(\underline{\varepsilon_2}) - H_{noise}(\underline{\varepsilon_2} \mid \underline{\varepsilon_1})$

[Equation 35]

where $H(Y|X)$ denotes the entropy of Y conditioned on X.

Using Eqs. 34 and 35, the joint entropy is rearranged as Eq. 36.

$H_{noise}(\underline{\varepsilon_1}, \underline{\varepsilon_2}) = H_{noise}(\underline{\varepsilon_2}) + H_{noise}(\underline{\varepsilon_1} \mid \underline{\varepsilon_2})$ $= H_{noise}(\underline{\varepsilon_1}) + H_{noise}(\underline{\varepsilon_2} \mid \underline{\varepsilon_1})$

[Equation 36]

To calculate Eq. 36, the variance of each element in Eq. 33 is required. Assuming strong constant phasor plus a weak random phasor sum for each matrix element, the variances are derived as Eqs. 37 to 40.

$\text{Var}(\varepsilon_{1H})=\text{Var}(ha-fc)=\text{Var}(h)\text{Var}(a)+\text{Var}(h)\{E(a)\}^2+\{E(h)\}^2\text{Var}(a)+\text{Var}(f)\text{Var}(c)+\text{Var}(f)\{E(c)\}^2+\{E(f)\}^2\text{Var}(c)$ [Equation 37]

$\text{Var}(\varepsilon_{1V})=\text{Var}(-ga+ec)=\text{Var}(g)\text{Var}(a)+\text{Var}(g)\{E(a)\}^2+\{E(g)\}^2\text{Var}(a)+\text{Var}(e)\text{Var}(c)+\text{Var}(e)\{E(c)\}^2+\{E(e)\}^2\text{Var}(c)$ [Equation 38]

$$\text{Var}(\epsilon_{2H}) = \text{Var}(hb-fd) = \text{Var}(h)\text{Var}(b) + \text{Var}(h)\{E(b)\}^2 + \{E(h)\}^2 \text{Var}(b) + \text{Var}(f)\text{Var}(d) + \text{Var}(f)\{E(d)\}^2 + \{E(f)\}^2 \text{Var}(d) \quad \text{[Equation 39]}$$

$$\text{Var}(\epsilon_{2V}) = \text{Var}(-gb+ed) = \text{Var}(g)\text{Var}(b) + \text{Var}(g)\{E(b)\}^2 + \{E(g)\}^2 \text{Var}(b) + \text{Var}(e)\text{Var}(d) + \text{Var}(e)\{E(d)\}^2 + \{E(e)\}^2 \text{Var}(d) \quad \text{[Equation 40]}$$

where Var(X) and E(X) denote variance and an expected value of X, respectively.

Conditional variances that are necessary to calculate Eq. 36 are derived as Eqs. 41 to 44.

$$\text{Var}(\epsilon_{1H}|\underline{\epsilon_2}) = \{E(h)\}^2 \text{Var}(a) + \{E(f)\}^2 \text{Var}(c) \quad \text{[Equation 41]}$$

$$\text{Var}(\epsilon_{1V}|\underline{\epsilon_2}) = \{E(g)\}^2 \text{Var}(a) + \{E(e)\}^2 \text{Var}(c) \quad \text{[Equation 42]}$$

$$\text{Var}(\epsilon_{2H}|\underline{\epsilon_1}) = \{E(h)\}^2 \text{Var}(b) + \{E(f)\}^2 \text{Var}(d) \quad \text{[Equation 43]}$$

$$\text{Var}(\epsilon_{2V}|\underline{\epsilon_1}) = \{E(g)\}^2 \text{Var}(b) + \{E(e)\}^2 \text{Var}(d) \quad \text{[Equation 44]}$$

Using the ensemble average of the absolute square of individual elements in Eq. 33 and the variances in Eqs. 37 to 44, we derive Eqs. 45 to 48.

$$P^{(\varepsilon_1)} = \frac{\sqrt{\left(\overline{|\varepsilon_{1H}|^2} - \overline{|\varepsilon_{1V}|^2}\right)^2 + 4\left(\overline{|\varepsilon_{1H}|^2} - \text{Var}(\varepsilon_{1H})\right)\left(\overline{|\varepsilon_{1V}|^2} - \text{Var}(\varepsilon_{1V})\right)}}{\overline{|\varepsilon_{1H}|^2} + \overline{|\varepsilon_{1V}|^2}} \quad \text{[Equation 45]}$$

$$P^{(\varepsilon_2)} = \frac{\sqrt{\left(\overline{|\varepsilon_{2H}|^2} - \overline{|\varepsilon_{2V}|^2}\right)^2 + 4\left(\overline{|\varepsilon_{2H}|^2} - \text{Var}(\varepsilon_{2H})\right)\left(\overline{|\varepsilon_{2V}|^2} - \text{Var}(\varepsilon_{2V})\right)}}{\overline{|\varepsilon_{2H}|^2} + \overline{|\varepsilon_{2V}|^2}} \quad \text{[Equation 46]}$$

$$P^{(\varepsilon_1|\varepsilon_2)} = \frac{\sqrt{\left(\overline{|\varepsilon_{1H}|^2} - \overline{|\varepsilon_{1V}|^2}\right)^2 + 4\left(\overline{|\varepsilon_{1H}|^2} - \text{Var}(\varepsilon_{1H}|\underline{\varepsilon_2})\right)\left(\overline{|\varepsilon_{1V}|^2} - \text{Var}(\varepsilon_{1V}|\underline{\varepsilon_2})\right)}}{\overline{|\varepsilon_{1H}|^2} + \overline{|\varepsilon_{1V}|^2}} \quad \text{[Equation 47]}$$

$$P^{(\varepsilon_2|\varepsilon_1)} = \frac{\sqrt{\left(\overline{|\varepsilon_{2H}|^2} - \overline{|\varepsilon_{2V}|^2}\right)^2 + 4\left(\overline{|\varepsilon_{2H}|^2} - \text{Var}(\varepsilon_{2H}|\underline{\varepsilon_1})\right)\left(\overline{|\varepsilon_{2V}|^2} - \text{Var}(\varepsilon_{2V}|\underline{\varepsilon_1})\right)}}{\overline{|\varepsilon_{2H}|^2} + \overline{|\varepsilon_{2V}|^2}} \quad \text{[Equation 48]}$$

The von Neumann entropy $H_{noise}$ of the noise component of the local Jones matrix in Eq. 36 is calculated using Eqs. 24, 25, and 45-48. If each factor of the product at the second term in the square root of the numerator in Eqs. 45-48 has a negative value, $P^{(1)}$ can become out of the defined range from 0 to 1. To avoid the undefined range, if each factor of the product at the second term in the square root of the numerator in Eqs. 45-48 has a negative value, it can be replaced to 0, and then Eqs. 45-48 can be calculated.

In the embodiments, depth-dependent noise variance of each matrix element can be calculated applying polynomial fit to the averaged noise power of A-scans without placing a scattering sample. This measurement of the noise floor and the calculation of the parameters can be performed at any timing, for example, during the manufacturing the device, at a certain predetermined time automatically such as after turning on the device, and before or after the measurement of the sample by operating an optical shutter or an optical scanner under a condition that the light from the sample is not detected.

Next, a case where a number of samples for the ensemble average of the covariance matrix is small, is considered. The entropy can be underestimated if the number of samples for ensemble average of the covariance matrix is small. To mitigate the underestimation of the entropy, asymptotic quasi maximum likelihood estimator (AQ-MLE) of the eigenvalues is used. The eigenvalues of the ensemble averaged covariance matrix are estimated by the AQ-MLE as Eq. 49.

$$\hat{l}_i = \lambda_i - \frac{\lambda_i}{n} \sum_{j=1, j \neq i}^{m} \frac{\lambda_j}{\lambda_i - \lambda_j} - O(n^{-1}), \; i = 1, 2, \ldots, m \quad \text{[Equation 49]}$$

where $\hat{l}_i$ is the estimated i-th eigenvalue, $\lambda_i$ is the i-th eigenvalue calculated by a finite number of samples in the ensemble average, n is the number of samples, and m=4 because of the dimension of our covariance matrix. The term $O(n^{-1})$ indicates an approximation order, and is ignored in the practical calculation.

The estimated eigenvalues by Eq. 49 are normalized and used to estimate the entropy as Eq. 50.

$$\hat{H} = \sum_{i=1}^{4} -\hat{l}'_i \log_4 \hat{l}'_i, \; \hat{l}'_i = \frac{\hat{l}_i}{\sum_{i=1}^{4} \hat{l}_i} \quad \text{[Equation 50]}$$

where $\hat{H}$ is the estimated von Neumann entropy.

Here, Cloude-Pottier decomposition that has been used in the above is discussed. Cloude-Pottier decomposition can be used as an image filter. The raw data for this operation can be either three-dimensional volumetric data, data with repeated scan at a same region on the sample, or these combinations. For example, a coherent Jones matrix filter can be applied to the data as the first step. In the second step, Cloude-Pottier decomposition can be applied. If this approach is applied to the data with a scan repeated for at least two times for a region of each B-scan or a region of three-dimension, an accuracy of the filtering can be enhanced. In this case, each filter in the first or second step can be applied either two- or three-dimensionally in space, temporarily, or these combinations. After that, Cloude-Pottier decomposition including the above-described eigenvalue decomposition may be applied. This approach of image filtering can be regarded as a kind of moving average.

As a kernel size of the coherent Jones matrix filter, for example, 3×1 pixels (axial×lateral) may be set. Alternately, as a kernel size of the coherent Jones matrix filter, for example, 7×11 pixels (axial×lateral) may be set. The kernel size is not necessarily a rectangular shape. It can be set to be an arbitrary shape spatially and temporarily. Arbitrary weight function, for example, Gaussian function, can be also applied to the kernel.

Further, since Jones matrix filter is mainly used for removing spatially small speckle noises and Cloude-Pottier decomposition is used to take local statistics larger than speckle, it is preferred to use larger kernel size of Cloude-Pottier decomposition than that of the coherent Jones matrix filter. However, the implementation is not necessarily limited to these conditions.

In the other embodiment, an arbitrary threshold value can be set to the signal intensity of the raw data, and the pixels having a signal intensity equal to or smaller than the threshold value can be excluded from the raw data through the image filtering. In this way, the calculation process can speed up. In addition, the pixels having a signal intensity equal to or smaller than the threshold value, can be masked in an arbitrary color, e.g., black. With this masking, it is possible to focus only on a region where the signals and information of the sample exist.

The phase retardation, optic axis, von Neumann entropy with noise-bias correction obtained by Cloude-Pottier decomposition, and von Nuemann entropy of the noise components can be imaged with arbitrary color maps. In addition, these images can be volume-rendered. Moreover, the signal intensity or signal intensity with thresholding can be used for an opacity of the volume rendering.

Although Jones matrix has been used as the raw data for the analysis above, Jones vector that is a subspace of the Jones matrix is also held by the same theory. Namely, it is possible to derive von Neumann entropy by regarding the Jones vector as 1×2 target vector, calculating an ensemble average of 2×2 covariance matrix from Eq. 8, estimating Jones vector using Cloude-Pottier decomposition, and using Eq. 24. In addition, it is possible to show von Neumann entropy that only represents the polarization property of the sample by calculating DOPU of the subspace using Eqs. 27 to 30 and von Neumann entropy $H_{noise}$ of the noise components in the subspace using Eqs. 24 and 25, subtracting $H_{noise}$ from the measured von Neumann entopy. In this way, the randomness of the polarization property of the sample and/or the light scattered by the sample.

In a case of the Jones vector, it is also possible to set the kernel size of the image filtering and the visualization method of the image as well as the case of the Jones matrix described above. Since Jones vector can be measured by detecting at least two different polarization components, this approach contributes simplifying the data processing algorithm and the hardware. For example, by splitting the interfered light to two orthogonal polarization components using, e.g., a polarizing beam splitter or a Wollaston prism, building a polarization-diverse detection system that detects the two orthogonal polarization components individually, an OCT system that can measure Jones vector can be made, thereby enabling to obtain von Neumann entropy as described above.

Here, Cloude-Pottier decomposition is based on a mathematical theorem that the covariance matrix C follows a complex Wishart distribution, and Z and T are the maximum likelihood estimator of C. It is possible to derive various parameters using this theorem, such as the phase retardation, optic axis, von Neumann entropy and diattenuation from Jones matrix Li and eigenvalues λi that are derived by decomposing the covariance matrix. In addition to distributions of these parameters, multivariate distribution itself like the complex Wishart distribution includes the polarization property of the biological tissues and nonbiological materials, enabling to use the distributions for segmentation and classification of the biological tissues and nonbiological materials that have different polarization properties. Namely, multivariate space can be created using a part or all of distributions of the above parameters and multivariate distribution, and then the measured data of the biological tissues and/or nonbiological materials can be segmented or classified by supervised learning, e.g., neural network, support vector machine, decision tree, random forest, naïve Bayes classifier and/or unsupervised learning, e.g., clustering algorithms.

EXAMPLE

Experimental examples to evaluate the method to correct noise components of von Neumann entropy are shown in the following. Hereinafter, measurement results of three static samples are described; a glass plate, quarter waveplate (EWP) at 633 nm and quarter waveplate at 1310 nm (QWP). Since the QWP at 633 nm is close to a one-eighth waveplate (EWP) at 1310 nm, it is called an EWP for expedience. A PS-OCT with a center wavelength of 1297 nm is used for the experiment.

Figure 5:
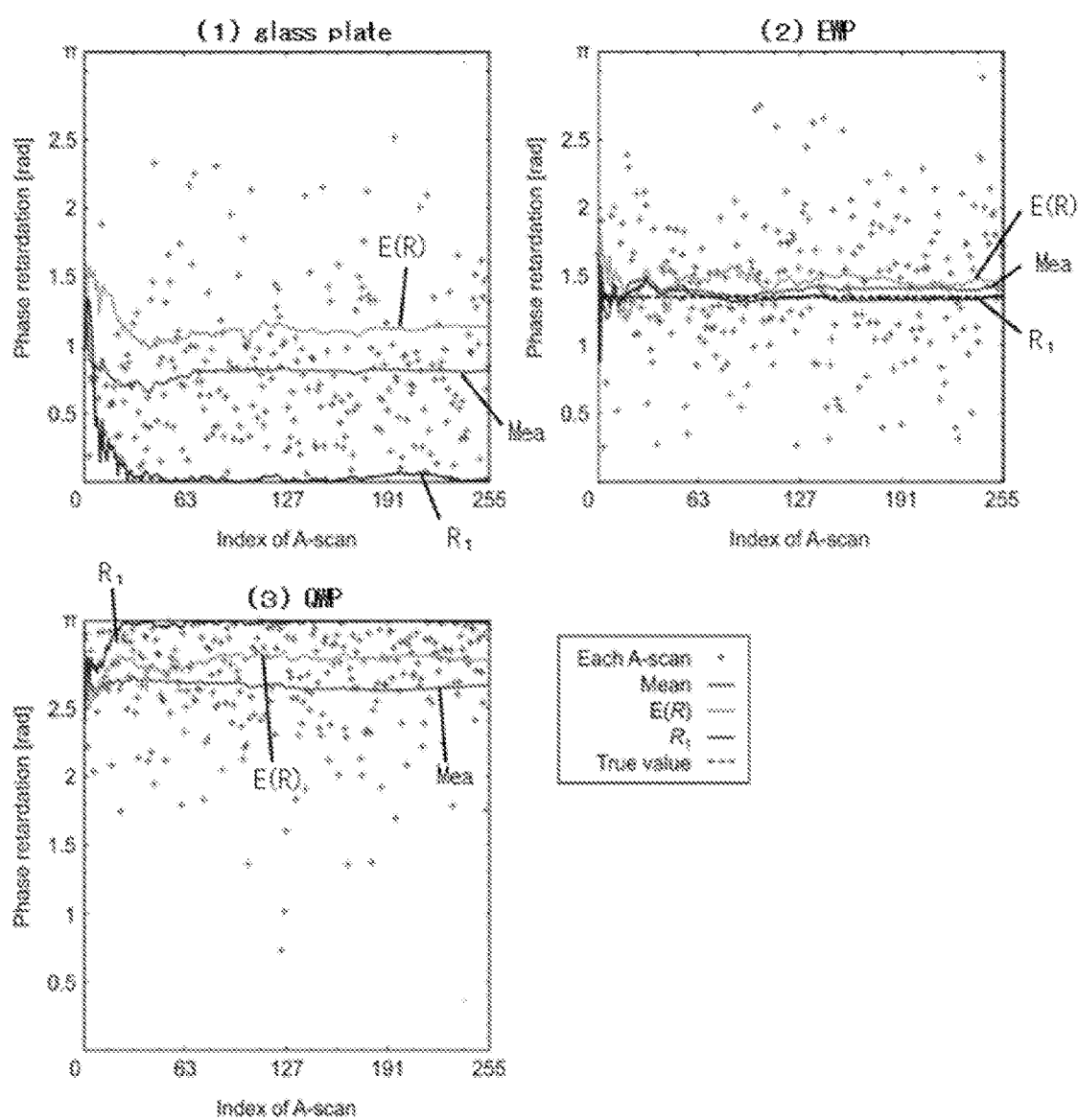
FIG. 5 is a graph showing results of example 1 according to the present disclosure.

As an experimental example 1, the local Jones matrices between the front and back surfaces of the above static samples were measured, and the double-pass phase retardation was estimated by the mean, the expected value E(R) in Eq. 19, the estimated value $R_1$ in Eq. 18. The results of the experimental example 1 were shown in FIG. 5. In FIG. 5, the plots of the glass plate, the EWP and the QWP were the phase retardation calculated from each single A-scan, respectively. The plots of mean, E(R) and $R_1$ were calculated using all 0 to n-th A-scans for the estimation. The measured von Neumann entropies of FIGS. 5(1), (2) and (3) were 0.74, 0.62 and 0.66, respectively. The effective signal-to-noise ratios (ESNRs) were 3.50, 5.27 and 4.88 dB, respectively.

In FIGS. 5(1) and (3), the true values were at the lower and upper limits of the measurable range, respectively. In these cases, the mean and E(R) were biased. The biases of the mean and E(R) were because of an asymmetric distribution of the phase retardation and the noise components in $R_i$ (I≥2), respectively. The biases of the mean and E(R) in FIG. 5(2) were smaller than FIGS. 5(1) and (3), because the distribution of the phase retardation was nearly symmetric. In contrast, $R_1$ converged on the true value in all of FIGS. 5($a$), ($b$) and ($c$). Hence, $R_1$ would be the most effective way of unbiased estimation even if the SNR is low.

Since the optic axis was wrapped when the phase retardation of the sample is exactly π, as an experimental example 2, the EWP was measured to evaluate the estimation of the optic axis when the phase retardation was not π. The orientation of the optic axis was set from 0 to 180 degrees with a 10-degree step, and the orientation was estimated by the eigenvector of $L_1$ in Cloude-Pottier decomposition. The eigenvector was converted to the Stokes parameters, and a relative orientation to 0 degree that used 800 A-scans for the ensemble average of the covariance matrix T was calculated. A wrapping over 90-degree orientation was unwrapped manually. The estimated optic axis orientation was shown in FIG. 6. To see the influence of the number of samples, the ensemble average of T was calculated using 8, 16, 32, 64 or 128 A-scans. This calculation was repeated in 800 A-scans to see the distributions of the estimation results. The entropy and the ESNR were 0.25 and 12.42 dB in average, respectively.

Figure 6:
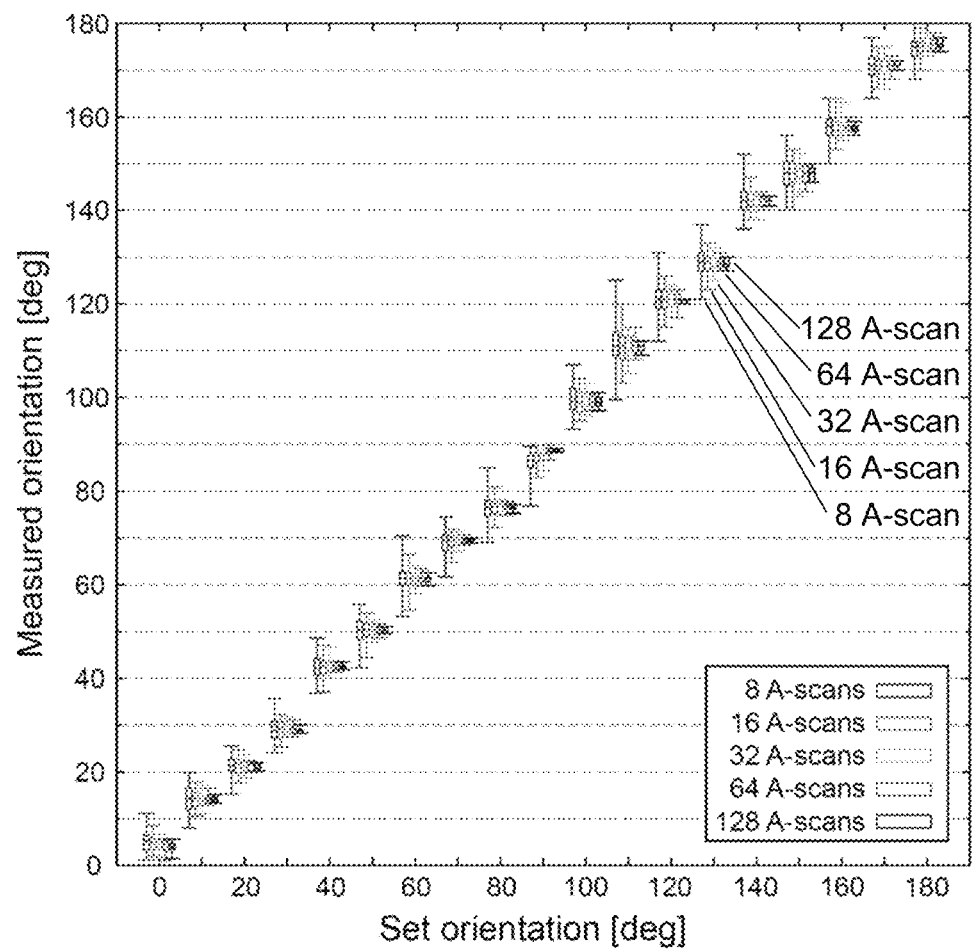
FIG. 6 is a graph showing results of example 2 according to the present disclosure.
Figure 7A:
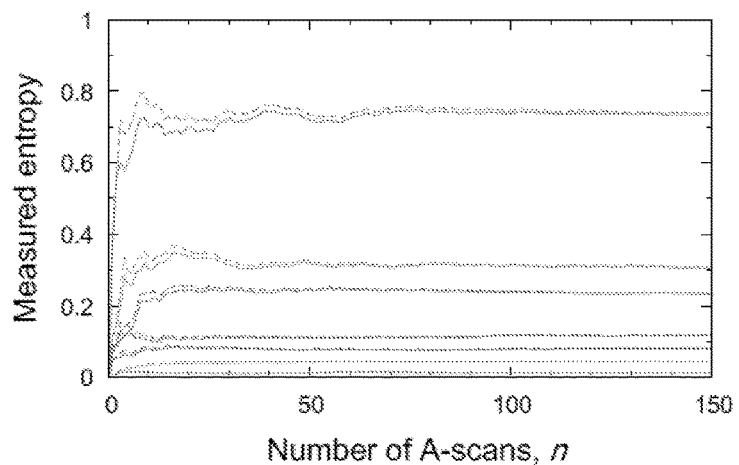
FIGS. 7A to 7F are graphs showing results of example 3 according to the present disclosure.
Figure 7B:
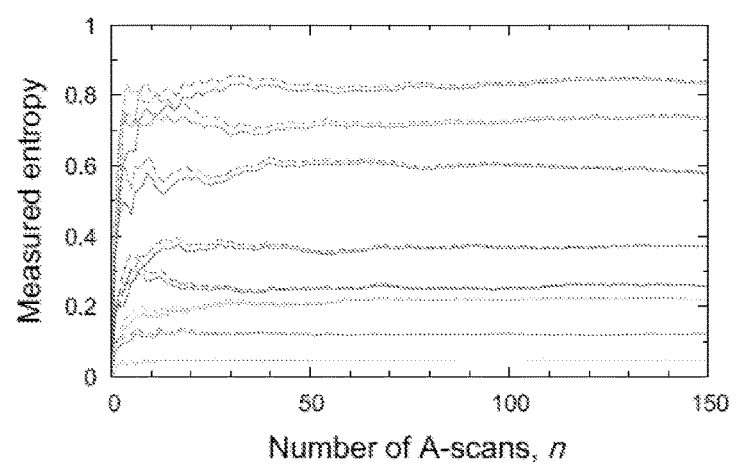
Figure 7C:
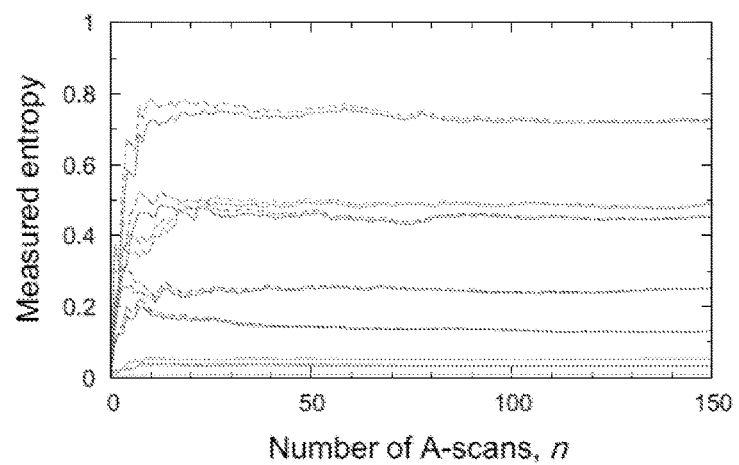
Figure 7D:
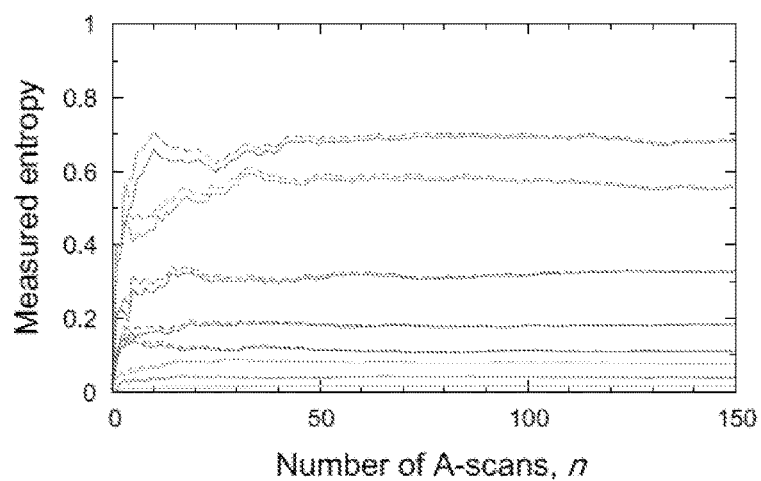
Figure 7E:
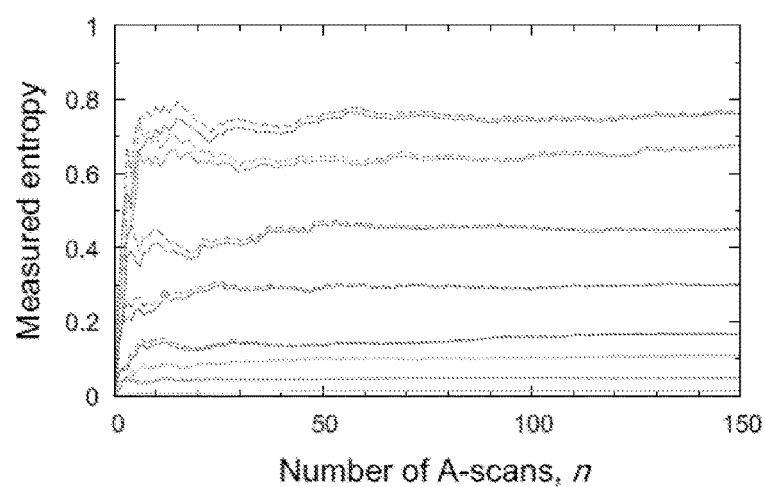
Figure 7F:
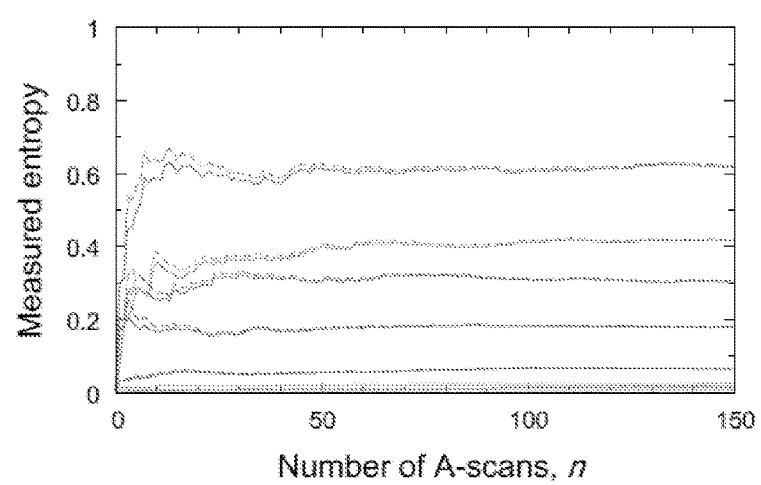

FIG. 6 clearly shows that by increasing the number of A-scans for the ensemble average of T in Cloude-Pottier decomposition, it gives a better estimation of the orientation with narrower distribution close to the set orientation of the Birefringence axis. Consequently, FIGS. 5 and 6 shows that the Jones matrix can be estimated by $L_1$ in Cloude-Pottier decomposition without the bias.

Next, as an experimental example 3, to evaluate the AQ-MLE shown in Eqs. 49 and 50, the glass plate, the EWP and the QWP were measured with settings of balanced and unbalanced SNRs. The settings were summarized in Table 1, where signal intensities relative to the maximum Jones-matrix element were shown.

speculated that a portion of the noise in the OCT channels might be correlated because of the depth-encoded configuration. When the entropy $\hat{H}$ is higher than 0.4, some plots showed the underestimation of $\hat{H}$ by $H_{noise}$. It would be because the assumption that signal intensity is sufficiently higher than noise intensity was not valid.

As an experimental example 5, $H_{noise}$ of the local Jones matrix was also calculated from the measured data with the same settings shown in Table 1. As described above, $H_{noise}$ was estimated and plotted with the entropy $\hat{H}$ in FIG. 9. For comparison, $H_{noise}(\epsilon_1)+H_{noise}(\epsilon_2)$, two equivalent calculation methods of $H_{noise}$ shown in Eq. 35 and ENSR were plotted.

Figure 9A:
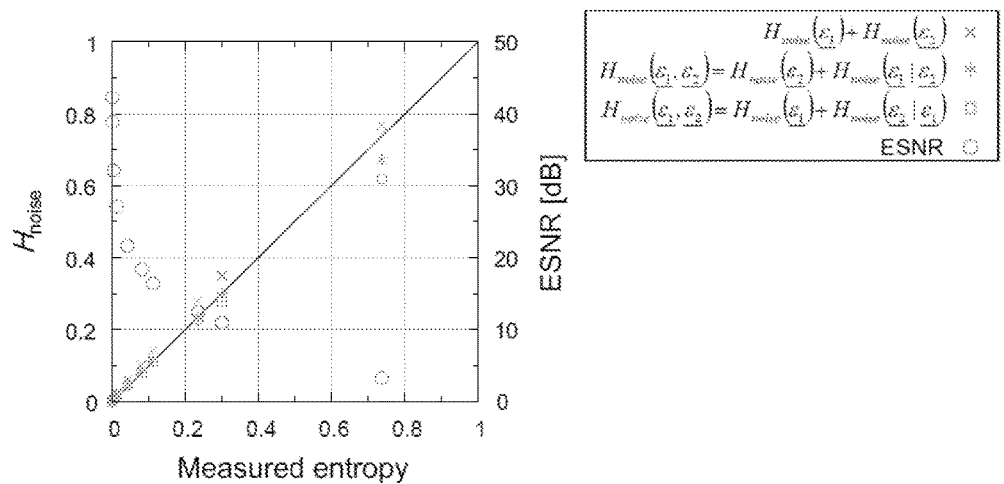
FIG. 9A to 9F are graphs showing results of example 5 according to the present disclosure.
Figure 9B:
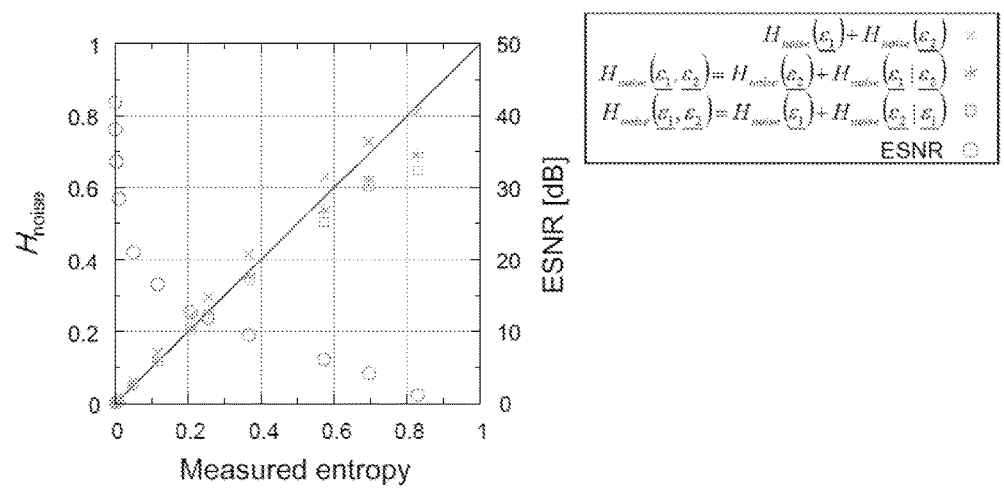
Figure 9C:
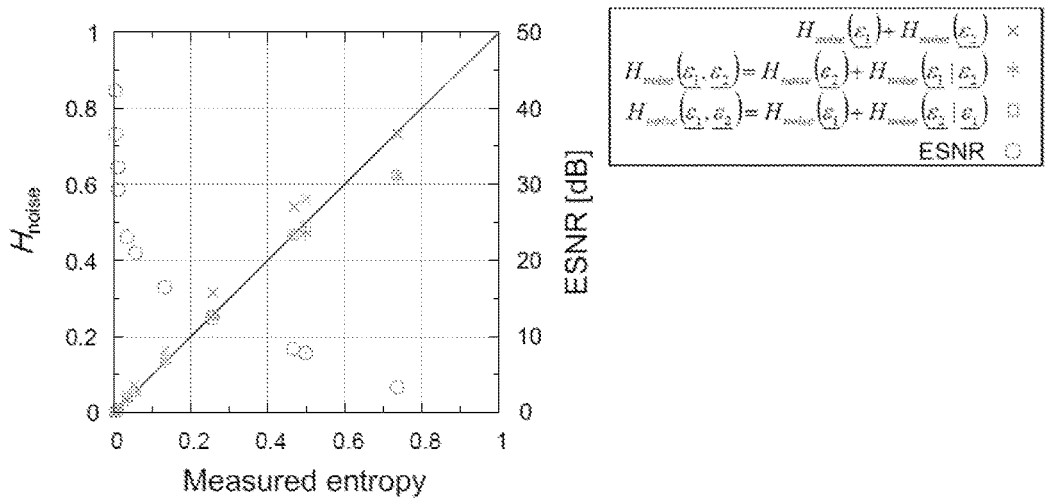
Figure 9D:
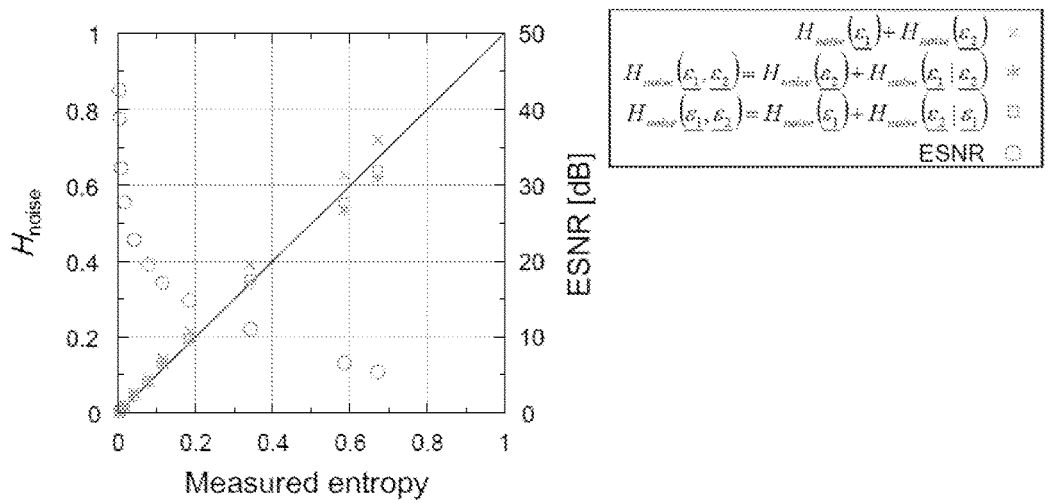
Figure 9E:
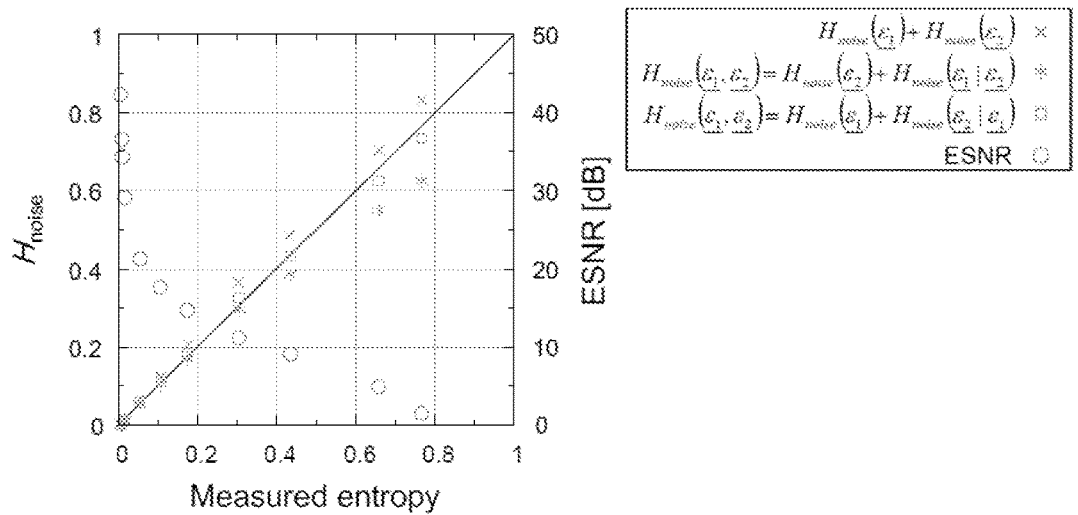
Figure 9F:
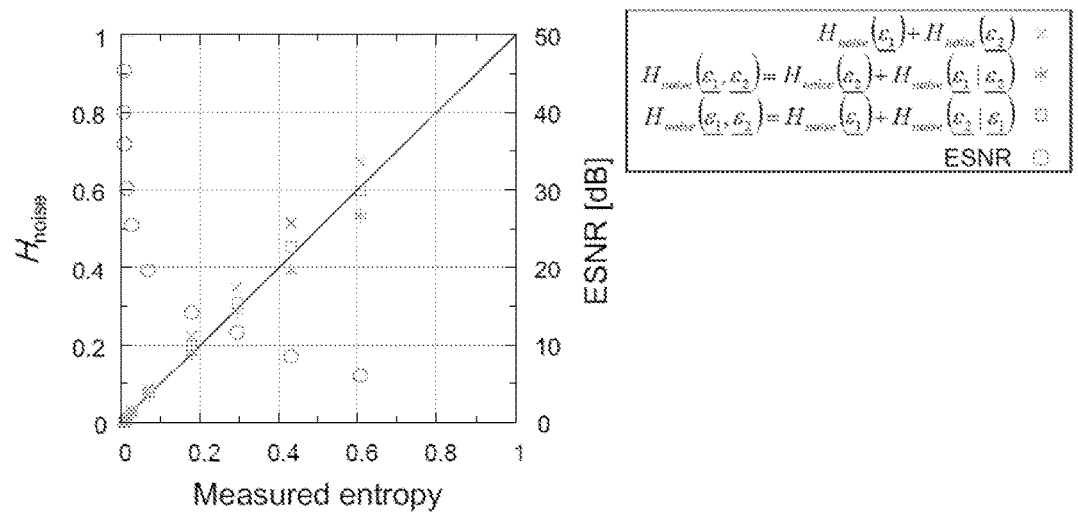

In FIG. 9, $H_{noise}(\epsilon_1)+H_{noise}(\epsilon_2)$ overestimated the entropy except high $\hat{H}$ in FIGS. 9(b) and (c). In contrast, both two

TABLE 1

| Sample | Balanced setting | | | | Unbalanced setting | | | |
|---|---|---|---|---|---|---|---|---|
| | Front surface [dB] | | Back surface [dB] | | Front surface [dB] | | Back surface [dB] | |
| | Setting (a) | | | | Setting (b) | | | |
| Glass plate | $\begin{bmatrix} -0.8 & -0.5 \\ -1.2 & 0 \end{bmatrix}$ | | $\begin{bmatrix} -0.2 & -0.1 \\ -0.9 & 0 \end{bmatrix}$ | | $\begin{bmatrix} -0.8 & -21.6 \\ -22.6 & 0 \end{bmatrix}$ | | $\begin{bmatrix} -0.3 & -20.9 \\ -21.7 & 0 \end{bmatrix}$ | |
| | Setting (c) | | | | Setting (d) | | | |
| EWP | $\begin{bmatrix} 0 & -2.7 \\ -2.3 & -2.4 \end{bmatrix}$ | | $\begin{bmatrix} -1.7 & -0.3 \\ 0 & -2.7 \end{bmatrix}$ | | $\begin{bmatrix} -0.8 & -3.9 \\ -4.7 & 0 \end{bmatrix}$ | | $\begin{bmatrix} 0 & -24.9 \\ -23.7 & -0.8 \end{bmatrix}$ | |
| | Setting (e) | | | | Setting (f) | | | |
| QWP | $\begin{bmatrix} -1.3 & -0.3 \\ 0 & -1.7 \end{bmatrix}$ | | $\begin{bmatrix} -1.2 & -1.9 \\ 0 & -4.1 \end{bmatrix}$ | | $\begin{bmatrix} 0 & -4.7 \\ -4.3 & -0.4 \end{bmatrix}$ | | $\begin{bmatrix} -22.2 & -0.4 \\ 0 & -21.7 \end{bmatrix}$ | |

To evaluate how the von Neumann entropy is converged in various settings, the measurements of the samples were performed in various signal intensities. The results were shown in FIG. 7. In FIG. 7, solid and dashed lines indicated the results without and with AQ-MLE, respectively. The horizontal axis shows a number of A-scans n used for the ensemble average of the covariance matrix T.

In FIG. 7, the entropy without AQ-MLE, H, was generally underestimated at small numbers of A-scans, n≤~20. The signals with high H had high variance and required more n till they converged. The underestimation was mitigated in the entropy with AQ-MLE, $\hat{H}$, at the small n, although the $\hat{H}$ still had remaining variance before the convergence. Both H and $\hat{H}$ converged to the same entropy at high n as expected in Eq. 50. As the signal attenuation was lower, H was lower and the difference between H and $\hat{H}$ was small even at small n. These observations were common in all of the samples and settings in Table 1, indicating that AQ-MLE was a robust and effective method to mitigate the underestimation of the entropy.

Next, as an experimental example 4, $H_{noise}$ of the measured cumulative Jones matrix at a certain depth was calculated from the measured data with the same settings shown in Table 1. As described above, using the signal intensities, $H_{noise}$ was estimated and the relationship with the von Neumann entropy $\hat{H}$ was plotted in FIG. 8.

Figure 8:
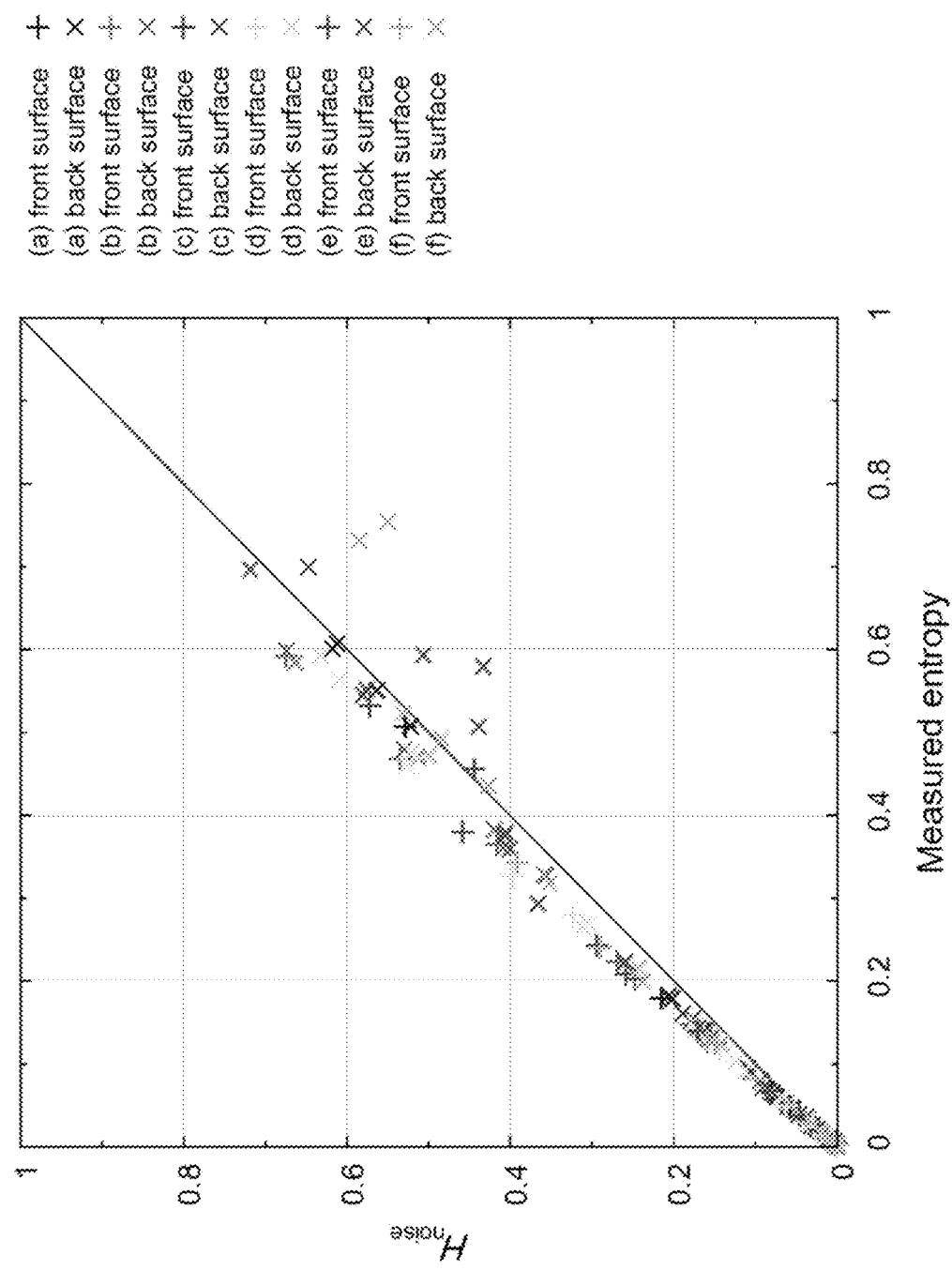
FIG. 8 is a graph showing results of example 4 according to the present disclosure.

In FIG. 8, $H_{noise}$ mostly corresponded to $\hat{H}$ with no dependence on the samples and the signal settings. Looking at the plots closely, however, $H_{noise}$ slightly overestimated $\hat{H}$. Although the reason of the overestimation is unclear, it is methods of $H_{noise}$ in Eq. 35 matched well with $\hat{H}$. The exception was at high $\hat{H}$ over ~0.5, where $H_{noise}$ underestimated $\hat{H}$. This would be also because the assumption of strong constant phasor plus a weak random phasor sum was not valid.

The embodiments of the invention were described in detail. The invention is not limited by the specific descriptions in the embodiments. Various changes can be applied to the embodiments as long as they do not deviate from the purport of the invention.

For example, the optical system of the OCT device may be configured in various ways, which is not limited to the configuration in FIG. 1. For example, a configuration in FIG. 10 may be also used. In the case of the OCT device in FIG. 10, plural tomographic images at the same location of the sample can simultaneously be acquired without reducing the axial measurement range for sampling of the two frequency-multiplexed interferometric components.

Namely, two measurement light with different optical path lengths are created, superposed and illuminates the sample. The reflected light from the sample is split by 321 to 332. They are combined and interfered with two different reference light with different optical path lengths at the interference units 360 and 370. The two interfered light were detected by two optical interference detectors 380 and 390, and two interferometric signals were generated. In the case of this configuration of the OCT device, the invention is also applicable.

Figure 10:
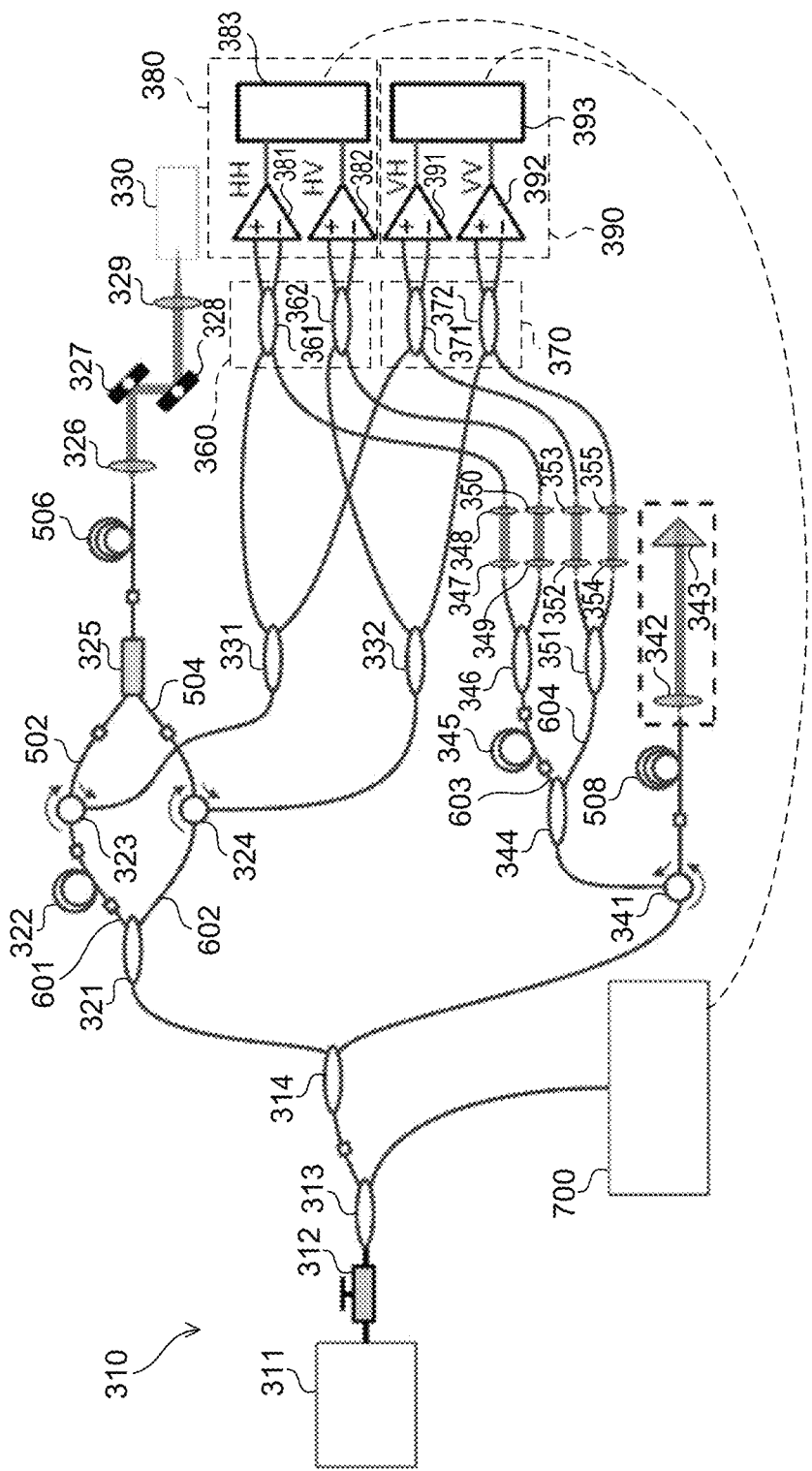
FIG. 10 is a diagram showing a configuration of an optical system of an optical coherence tomographic device of variant.

In the configuration of FIG. 10, two measurement light with a certain difference of the optical path lengths was configured to be generated. However, the generated measurement light are not limited to be two. Three or more measurement lights with optical path length differences can also be generated. For example, in a case of three measurement light with different optical path lengths, three reference light that corresponds to these measurement light may be generated, and three interference units and three interference detectors that correspond to individual optical path lengths may be configured.

What is claimed is:

1. An optical coherence tomographic device configured to acquire a tomographic image of a subject by using an optical interferometry, the optical coherence tomographic device comprising:
a detector configured to detect interference light acquired by the optical interferometry, and to output an interference signal of the interference light; and
a processor configured to calculate von Neumann entropy of noise components by using the noise components and signal intensities of the interference signals corresponding to at least one interference light detected by the detector, wherein the processor is configured to: calculate von Neumann entropy of the interference signal; and to calculate von Neumann entropy that indicates a polarization property of the subject by removing the von Neumann entropy of noise components from the calculated von Neumann entropy of the interference signal.

2. The optical coherence tomographic device of claim 1, wherein the von Neumann entropy of noise components is calculated based on a polarization property accumulated along a depth direction of the subject.

3. The optical coherence tomographic device of claim 2, wherein the polarization property accumulated along the depth direction of the subject is characterized by at least one of Jones matrix, Mueller matrix, Jones vector and Stokes vector.

4. The optical coherence tomographic device of claim 1, wherein the detector is configured to; divide the interference light into at least two different polarization components; and to detect each of the polarization components of the interference light.

5. The optical coherence tomographic device of claim 1, wherein the von Neumann entropy of noise components is calculated based on a polarization property localized along a depth direction of the subject.

6. The optical coherence tomographic device of claim 5, wherein the polarization property localized along the depth direction of the subject is characterized by at least one of Jones matrix, Mueller matrix, Jones vector and Stokes vector.

7. An optical coherence tomographic device configured to acquire a tomographic image of a subject by using an interferometry, the optical coherence tomographic device comprising:
a detector configured to detect interference light acquired by the optical interferometry, and to output an interference signal of the interference light; and
a processor configured to calculate covariance matrix that indicates a polarization property of the subject based on the interference signal outputted by the detector, and to calculate von Neumann entropy based on the calculated covariance matrix,
wherein the processor is configured to, when a number of samples of an ensemble average of the covariance matrix to be used for calculation is insufficient, correct an eigenvalues of the ensemble averaged covariance matrix, and calculate the von Neumann entropy by using the corrected eigenvalues.

8. An optical coherence tomographic device configured to acquire a tomographic image of a subject by using an optical interferometry, the optical coherence tomographic device comprising:
a detector configured to detect interference light acquired by the optical interferometry, and to output an interference signal of the interference light; and
a processor configured: to measure Jones matrices that indicate a polarization property of the subject based on the interference signal outputted by the detector; perform the moving average process relative to covariance matrices of Jones matrices that has been subjected to the moving average process; and estimate the Jones matrix by using eigenvalue decomposition; and calculate von Neumann entropy by using the eigenvalue decomposition.

9. The optical coherence tomographic device of claim 8, further comprising a scanner configured to scan measurement light,
wherein the scanner is configured to scan the subject with the measurement light such that three-dimensional volume data of the subject is acquired for acquiring the measured Jones matrices.

10. The optical coherence tomographic device of claim 8, further comprising a scanner configured to scan measurement light,
wherein the scanner is configured to scan a predefined region of the subject with the measurement light at least two times for acquiring the measured Jones matrices.

11. The optical coherence tomographic device of claim 8, further comprising a scanner configured to scan measurement light,
wherein the scanner is configured to scan the three-dimensional regions of the subject with the measurement light at least two times for acquiring the measured Jones matrices.

12. The optical coherence tomographic device of claim 8, wherein the processor is configured to: set a threshold value based on a signal intensity of the measured Jones matrices; and perform the moving average process of the measured Jones matrices by using only pixels that have a signal intensity equal to or greater than the threshold value.

13. The optical coherence tomographic device of claim 8, wherein the processor is configured to set a threshold value based on a signal intensity of raw data of the measured Jones matrices, and perform the moving average process of the covariance matrix by using only pixels that have a signal intensity equal to or larger than the threshold value.

14. The optical coherence tomographic device of claim 8, wherein the processor is configured to: set a threshold value based on a signal intensity of raw data of the measured Jones matrices; and output an image in which pixels that have a signal intensity equal to or smaller than the threshold value are masked in an arbitrary color.

* * * * *